(12) United States Patent
Farran et al.

(10) Patent No.: US 11,696,880 B2
(45) Date of Patent: *Jul. 11, 2023

(54) SKIN TIGHTENING COMPOSITIONS AND METHODS OF USE

(71) Applicant: L'OREAL, Paris (FR)

(72) Inventors: Alexandra Jane Elisa Farran, Dayton, NJ (US); Anne-Laure Suzanne Bernard, New York, NY (US); Prabhjot K. Saini, Avenel, NJ (US); Cynthia Ghobril, Paris (FR); Julie Martin-Besnardiere, Aulnay-sous-Bois (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/731,188

(22) Filed: Dec. 31, 2019

(65) Prior Publication Data

US 2021/0196586 A1 Jul. 1, 2021

(51) Int. Cl.

| | | |
|---|---|---|
| A61Q 19/08 | (2006.01) |
| A61Q 19/00 | (2006.01) |
| A61K 8/25 | (2006.01) |
| A61K 8/31 | (2006.01) |
| A61K 8/891 | (2006.01) |
| A61K 8/90 | (2006.01) |
| A61K 8/88 | (2006.01) |
| A61K 8/00 | (2006.01) |
| A61K 8/96 | (2006.01) |
| A61K 8/86 | (2006.01) |
| A61K 8/28 | (2006.01) |
| A61K 8/27 | (2006.01) |
| A61K 8/26 | (2006.01) |
| A61K 8/06 | (2006.01) |
| A61K 8/04 | (2006.01) |
| A61K 8/19 | (2006.01) |

(52) U.S. Cl.
CPC .............. *A61K 8/25* (2013.01); *A61K 8/044* (2013.01); *A61K 8/064* (2013.01); *A61K 8/19* (2013.01); *A61K 8/26* (2013.01); *A61K 8/27* (2013.01); *A61K 8/28* (2013.01); *A61K 8/31* (2013.01); *A61K 8/86* (2013.01); *A61K 8/88* (2013.01); *A61K 8/891* (2013.01); *A61K 8/965* (2013.01); *A61Q 19/08* (2013.01); *A61K 2800/48* (2013.01)

(58) Field of Classification Search
CPC .. A61K 2300/00; A61K 8/8152; A61K 8/891; A61K 2800/594; A61K 8/25; A61K 2800/10; A61K 8/31; A61K 2800/43; A61K 8/585; A61K 8/8117; A61K 8/8147; A61K 8/89; A61K 8/064; A61K 8/29; A61K 8/06; A61K 2800/30; A61K 2800/48; A61K 2800/31; A61K 8/062; A61K 8/90; A61K 2800/262; A61K 8/88; A61K 8/04; A61K 8/8111; A61K 8/8182; A61Q 19/08; A61Q 19/00

See application file for complete search history.

(56) References Cited

U.S. PATENT DOCUMENTS

| | | | |
|---|---|---|---|
| 4,599,379 A | 7/1986 | Flesher et al. |
| 4,628,078 A | 12/1986 | Glover et al. |
| 4,835,206 A | 5/1989 | Farrar et al. |
| 4,849,484 A | 7/1989 | Heard |
| 5,100,660 A | 3/1992 | Hawe et al. |
| 7,470,725 B2 | 12/2008 | Schwertfeger et al. |
| 9,918,925 B2 | 3/2018 | Debaud et al. |
| 2006/0127424 A1* | 6/2006 | Asano | A61K 8/0279 424/401 |
| 2006/0263308 A1* | 11/2006 | Brown | A61Q 1/02 424/59 |
| 2011/0171148 A1* | 7/2011 | Jones | A61Q 17/04 424/59 |
| 2012/0282188 A1 | 11/2012 | Feltin et al. |
| 2015/0342845 A1* | 12/2015 | Hwang | A61K 8/375 424/60 |
| 2017/0189288 A1 | 7/2017 | Chiou et al. |
| 2017/0189299 A1* | 7/2017 | Manning | A61K 8/26 |
| 2017/0183315 A1 | 7/2017 | Bernard et al. |
| 2017/0036068 A1 | 12/2017 | Debeaud et al. |
| 2017/0360682 A1 | 12/2017 | Debeaud et al. |
| 2018/0015023 A1 | 1/2018 | Bernard et al. |
| 2018/0028420 A1 | 2/2018 | Li et al. |
| 2018/0311138 A1 | 11/2018 | Huynh et al. |

FOREIGN PATENT DOCUMENTS

| | | | | |
|---|---|---|---|---|
| EP | 0228868 A2 | 7/1987 |
| EP | 0963751 A2 | 12/1999 |
| EP | 1411069 A2 | 4/2004 |
| WO | 2003045337 A2 | 6/2003 |
| WO | 2004055081 A2 | 7/2004 |
| WO | WO-2016100690 A1 * | 6/2016 | ............... A61K 8/29 |

* cited by examiner

*Primary Examiner* — Tracy Liu
(74) *Attorney, Agent, or Firm* — Polsinelli PC

(57) ABSTRACT

A skin tightening composition including about 2 to about 35 wt. % of at least one thickener selected from polyamide-8, styrene ethylene/propylene copolymer, nylon-611/dimethicone crosspolymer, VP/EICOSENE copolymer, fumed silicas, hydrophobically modified silica, silica silylate, clays and a combination thereof; about 1.5 to about 13 wt. % of at least one filler; about 5 to about 45 wt. % of at least one hydrophobic film former; and about 20 to about 85 wt. % of at least one volatile hydrocarbon, wherein a weight ratio of the at least one hydrophobic film former c) to the at least one thickener a) is 1:2 to 8:1 (hydrophobic film former c):thickener a)), and all weight percentages are based on the total weight of the skin tightening composition.

5 Claims, No Drawings

SKIN TIGHTENING COMPOSITIONS AND METHODS OF USE

FIELD OF THE DISCLOSURE

The present disclosure relates to skin tightening compositions for application to the skin for providing an instantaneous and dramatic improvement to the appearance of skin, for example, by reducing the appearance of wrinkles, eye bags, pores, and skin imperfections such as scarring, dark spots (and uneven skin tone), dark circles, and roughness.

BACKGROUND

Skin produces less collagen and elastin as it ages. For example, after the age of twenty, a person (human) produces about 1 percent less collagen in the skin each year. As a result, the skin becomes thinner and more fragile. Inevitably, wrinkles, crow's feet, age-spots, eye bags, and the like, begin to form.

Consumers often wish to improve the appearance of such age-related skin imperfections, preferably with instantaneous results. Many consumer products and procedures devoted to hiding and reducing wrinkles are available. Some products and procedures are simple and inexpensive, for example, applying make-up, particularly a primer or colored foundation, to cover the skin (and thereby cover and/or fill the wrinkles and provide a smoother look). Far more expensive and drastic procedures, such as surgical face lifts and Botox® injections, are also used to reduce the appearance of wrinkles. However, many consumers either cannot afford, or do not wish, to undergo such drastic cosmetic procedures. There are a number of lotions and creams which are formulated to hydrate the skin and make it more supple, thereby reducing the appearance of wrinkles. Some of these products contain active ingredients, for example, niacinamide, that help repair and rejuvenate skin over time. Unfortunately, however, all of these products and procedures have drawbacks.

Make-up products are often visible, offer minimal texture benefits, and have no long-term lasting effect on the skin. After removal of the make-up, the skin looks the same as before the make-up was applied. Common skin care products can have chronic, acute or both effects on the skin. Hydration and optical effects are common acute benefits, but these benefits quickly wear-off over time.

Attempts have been made to develop new categories of products to improve the appearance of skin without the drawbacks of existing products and procedures. One such family of products can be generally classified as "adhesive, contractile film formers". Film formers are chemical compositions that when applied to skin, leave a pliable, cohesive and continuous covering. A select group of film formers are also adhesive to the skin and contractile.

SUMMARY OF THE DISCLOSURE

The instant disclosure is directed to skin tightening compositions for providing an instantaneous and dramatic improvement to the appearance of skin, e.g., by reducing the appearance of wrinkles, eye bags, pores, and skin imperfections such as scarring, dark spots (and uneven skin tone), dark circles, and roughness. The skin tightening compositions include a unique combination of thickener(s), filler(s), film former(s), and volatile hydrocarbons, which provide desirable properties after being applied to the skin. The inventors discovered that certain skin tightening compositions of the instant disclosure also exhibited excellent transparency, haze, and gloss characteristics after forming a film on a user's skin.

The skin tightening compositions typically include:
a) about 2 to about 35 wt. % of at least one thickener chosen from polyamide-8, styrene ethylene/propylene copolymer, nylon-611/dimethicone crosspolymer, VP/EICOSENE copolymer, fumed silicas, hydrophobically modified silica, silica silylate, clays and a combination thereof;
b) about 1.5 to about 13 wt. % of at least one filler;
c) about 5 to about 45 wt. % of at least one hydrophobic film former; and
d) about 20 to about 85 wt. % of at least one volatile hydrocarbon,
wherein a weight ratio of the at least one hydrophobic film former c) to the at least one thickener a) is 1:2 to 8:1 (hydrophobic film former c):thickener a)), and
wherein all weight percentages are based on the total weight of the skin tightening composition.

The skin tightening compositions may include about 3 to about 20 wt. % of at least one thickener, based on the total weight of the skin tightening composition. In at least one instance, the skin tightening composition includes at least one thickener selected from polyamide-8, styrene ethylene/propylene copolymer nylon-611/dimethicone crosspolymer, VP/EICOSENE copolymer, fumed silica, hydrophobically modified silica, silica silylate, clays and a combination thereof. The at least one filler is, preferably, silica silylate, nylon-12, cellulose, methacrylate crosspolymer, silicone powder, and a combination thereof.

The skin tightening compositions includes at least one hydrophobic film former that may be chosen from acrylic acid/isobutyl acrylates/isobornyl acrylate copolymer, trimethylsiloxysilicate, acrylates/isobornyl acrylate copolymer, norbornene/tris(trimethylsiloxy)silylnorbornene copolymer, acrylate/polytrimethyl siloxymethacrylate copolymer, C30-45 alkyldimethylsilylpolypropylsilsequioxane, trimethylsilsesquioxane, polypropylsilsesquioxane, acrylates/dimethicone copolymer, octylacrylamide/acrylates/butylaminoethyl methacrylate copolymer, VA/butyl maleate/isobornyl acrylate copolymer, acrylates/t-butylacrylamide copolymer, polyvinylpyrrolidone/vinyl acetate copolymer, triacontanyl PVP copolymer, acrylates/dimethylaminoethyl methacrylate copolymer, and a combination thereof. Preferably, the hydrophobic film former is acrylic acid/isobutyl acrylates/isobornyl acrylate copolymer, trimethylsiloxysilicate, acrylates/isobornyl acrylate copolymer, norbornene/tris(trimethylsiloxy)silylnorbornene copolymer, acrylates/polymethylsiloxymethacrylate copolymer, and a combination thereof.

Suitable volatile hydrocarbons that may be included in the skin tightening composition include isoparaffin, isohexadecane, isododecane, isodecane, undecane, tridecane, dodecane, isohexyl, isodecyl, neopentanoate, or a combination thereof.

In accordance with one aspect of the invention, the skin tightening composition may be formulated as an anhydrous composition. For example, the skin tightening composition may include 1 wt. % or less of water. In some instances, the skin tightening compositions include about 0 wt. % of water. The skin tightening composition may, additionally or alternatively, be free or essentially free of dimethicone crosspolymer.

According to another aspect of the invention, the skin tightening composition is an emulsion, such as a water-in-oil emulsion. The skin tightening composition may include about 1 to about 10 wt. % of at least one non-ionic surfactant. Suitable non-ionic surfactants include dimethicone (and) peg/ppg-18/18 dimethicone, lauryl peg-9 polydimethylsiloxyethyl dimethicone, cetyl peg/ppg-10/1 dimethicone, peg-30 dipolyhydroxystearate, polyglyceryl-4 diisostearate/polyhydroxystearate/sebacate, polyglyceryl-4 isostearate, polyglyceryl-2 dipolyhydroxystearate, and a combination thereof. In at least some instances, the non-ionic surfactant is chosen from dimethicone (and) peg/ppg-18/18 dimethicone, lauryl peg-9 polydimethylsiloxyethyl dimethicone, and a combination thereof.

Additionally, the skin tightening composition of claim may include about 0.5 to about 10 wt. %, e.g. about 1 to about 10 wt. %, of at least one dispersant. Non-limiting examples of dispersants include those chosen from olyoxyethylene glycol ethers or esters (POE/PEG ethers or esters) or polyoxypropylene glycol ethers or esters (PPG ethers or esters), from sugar ethers or esters, from glycerol or polyglycerol ethers or esters and from ethoxylated glyceride esters (POE glyceryl esters), polyhydroxystearic acid, or a combination thereof. In some cases the skin tightening composition includes pigments, such as inorganic pigments chosen from titanium dioxide, zirconium oxide, cerium oxide, zinc 10 oxide, iron oxide, mica, alumina, aluminum hydroxide, chromium oxide, manganese violet, ultramarine blue, chromium hydrate, ferric blue, aluminum powder, copper powder, silver powder, gold powder, barium sulfate, carbon black, and a mixture thereof.

DETAILED DESCRIPTION OF THE DISCLOSURE

The instant disclosure is directed to skin tightening compositions for providing an instantaneous and dramatic improvement to the appearance of skin, e.g., by reducing the appearance of wrinkles, eye bags, pores, and skin imperfections such as scarring, dark spots (and uneven skin tone), dark circles, and roughness. The inventors discovered that certain skin tightening compositions of the instant disclosure also exhibited excellent transparency, haze, and gloss characteristics after forming a film on a user's skin.

The skin tightening compositions typically include:
a) about 2 to about 35 wt. % of at least one thickener chosen from polyamide-8, styrene ethylene/propylene copolymer, nylon-611/dimethicone crosspolymer, VP/EICOSENE copolymer, fumed silicas, hydrophobically modified silica, silica silylate, clays and a combination thereof;
b) about 1.5 to about 13 wt. % of at least one filler;
c) about 5 to about 45 wt. % of at least one hydrophobic film former; and
d) about 20 to about 85 wt. % of at least one volatile hydrocarbon,
  wherein a weight ratio of the at least one hydrophobic film former c) to the at least one thickener a) is 1:2 to 8:1 (hydrophobic film former c):thickener a)), and
  wherein, all weight percentages are based on the total weight of the skin tightening composition.

The weight ratio of the hydrophobic film former c) to the at least one thickener a) may range from 1:2 to 8:1, 1:1.5 to 8:1, 1:1 to 8:1, 1:2 to 7:1, 1:2 to 6:1, 1:2 to 5:1, 1:2 to 4:1, 1:2 to 3:1, 1:2 to 2:1, or 1:2 to 1:1.

The skin tightening compositions may be formulated to be anhydrous or essentially anhydrous. For example, the skin tightening compositions may include 10% or less, 8% or less, 6 wt. % or less, 5 wt. % or less, 4 wt. % or less, 3 wt. % or less, 2 wt. % or less of water. In at least one instance, the skin tightening composition include 1 wt. % of less of water. In another instance, the skin tightening compositions include about 0 wt. % of water.

Advantageously, the skin tightening compositions may alternatively be formulated as an emulsion. Typically, the skin tightening compositions are formulated to be water-in-oil emulsions, however, the skin tightening compositions may be formulated to be a hydrophilic phase (e.g., alcohols, glycols, polyols, etc.) in oil phase emulsion or even as an oil-in-water emulsion.

The skin tightening compositions, which are in the form of an emulsion, typically include:
a) about 2 to about 35 wt. % of at least one thickener chosen from polyamide-8, styrene ethylene/propylene copolymer, nylon-611/dimethicone crosspolymer, VP/EICOSENE copolymer, fumed silicas, hydrophobically modified silica, silica silylate, clays, and a combination thereof;
b) about 1.5 to about 13 wt. % of at least one filler;
c) about 5 to about 45 wt. % of at least one hydrophobic film former;
d) about 20 to about 70 wt. % of at least one volatile hydrocarbon;
e) about 1 to about 10 wt. % of at least one non-ionic surfactant;
f) about 0.5 to about 10 wt. % of at least one dispersant; and
g) about 5 to about 60 wt. % of water;
  wherein a weight ratio of the at least one hydrophobic film former c) to the at least one thickener a) is 1:2 to 8:1 (hydrophobic film former c):thickener a)), and
  wherein the skin tightening composition is an emulsion, and all weight percentages are based on the total weight of the skin tightening composition.

The skin tightening compositions may be formulated to be free or essentially free of dimethicone crosspolymer. In some instances, the skin tightening composition includes 3 wt. % or less, 2 wt. % or less, or 1 wt. % or less of dimethicone crosspolymer. In another instance, the skin tightening compositions include about 0 wt. % of dimethicone crosspolymer. The skin tightening compositions may also be formulated to be free or essentially free of compounds including or formed of dimethicone crosspolymer. The skin tightening compositions may include 3 wt. % or less, 2 wt. % or less, or 1 wt. % or less of compounds including or formed of dimethicone crosspolymer. In at least one case, the skin tightening compositions include about 0 wt. % of compounds including or formed of dimethicone crosspolymer. Additionally or alternatively, the skin tightening compositions may be free or essentially free of silicone elastomers. In some instances, the skin tightening composition includes 3 wt. % or less, 2 wt. % or less, or 1 wt. % or about 0 wt. % of silicone elastomers.

The inventors discovered that certain skin tightening compositions of the instant disclosure exhibited excellent transparency, haze, and gloss characteristics after being applied to and/or forming a film on a user's skin. The transparency and the haze of the films formed from the skin tightening compositions were measured using a BYK Haze-Guard instrument as further discussed in the Examples. Preferably, the films formed from the skin tightening compositions exhibited a transparency of 90% or more, more preferably 92% or more, more preferably 93% or more, more preferably 94% or more, more preferably 95% or more, more preferably 96% or more, more preferably 97% or more, or more preferably 98% or more for non-pigmented skin tightening compositions. Additionally or alternatively, the films formed from the skin tightening compositions exhibited a haze of preferably at least 89% and up to 98% or more preferably at least 90% and up to 97% for non-pigmented skin tightening compositions.

The films formed from the skin tightening compositions preferably exhibited a gloss characteristic as measured at an angle of 60° of less than 12. For example, a BYK Glossmeter may be used to measure the gloss and mattness of the film formed from the skin tightening composition at an angle of 60°. In some instances, the gloss measurement at an angle of 60°, using a BYK Glossmeter, was preferably less than 10, more preferably less than 8, more preferably less than 7, more preferably less than 6, or more preferably less than 5.

Suitable components, such as those listed below, may be included or excluded from the formulations for the skin tightening compositions depending on the specific combination of other components, the form of the skin tightening compositions, and/or the use of the formulation (e.g., a lotion, gel, cream, spray, etc.).

Thickener(s)

The skin tightening composition includes at least one thickener selected from polyamide-8, styrene ethylene/propylene copolymer, and nylon-611/dimethicone crosspolymer, VP/EICOSENE Copolymer, fumed silicas, hydrophobically modified silica, silica silylate, clays, or a combination thereof. In at least one instance, the thickener(s) includes or is selected from polyamide-8, styrene ethylene/propylene copolymer, nylon-611/dimethicone crosspolymer, and a combination thereof. In at least one other instance, the thickener(s) includes or is selected from polyamide-8, styrene ethylene/propylene copolymer, and a combination thereof. For example, it may be desirable, in some instances, for the skin tightening composition to not have dimethicone crosspolymer and/or compounds including or formed of dimethicone crosspolymer, such as nylon-611/dimethicone crosspolymer.

The amount of thickeners in the skin tightening composition typically ranges from about 2 to about 35 wt. %, based on the total weight of the skin tightening composition. For example, the skin tightening composition may include thickeners in an amount of about 3 to about 35 wt. %, about 4 to about 35 wt. %, about 5 to about 35 wt. %, about 6 to about 35 wt. %, about 8 to about 35 wt. %, about 10 to about 35 wt. %, about 14 to about 35 wt. %, about 18 to about 35 wt. %, about 22 to about 35 wt. %, about 2 to about 25 wt. %; about 3 to about 25 wt. %, about 4 to about 25 wt. %, about 6 to about 25 wt. %, about 8 to about 25 wt. %, about 10 to about 25 wt. %, about 14 to about 25 wt. %, about 18 to about 25 wt. %; about 2 to about 20 wt. %, about 3 to about 20 wt. %, about 4 to about 20 wt. %, about 6 to about 20 wt. %, about 8 to about 20 wt. %, about 10 to about 20 wt. %, about 14 to about 20 wt. %; about 2 to about 15 wt. %, about 3 to about 15 wt. %, about 4 to about 15 wt. %, about 6 to about 15 wt. %, about 8 to about 15 wt. %, about 10 to about 15 wt. %, including all ranges and subranges, based on the total weight of the skin tightening composition.

The skin tightening compositions may include one or more additional thickening agents. The additional thickening agents may be mineral thickening agents or non-mineral thickening agents.

Mineral Thickening Agents

Mineral thickening agents are mineral based compounds that thicken or modify the viscosity of the skin tightening compositions. Non-limiting examples of additional mineral thickening agents include silica silylate, fumed silica, zeolite, natural clay, synthetic clay, kaolin, hectorite, organically modified hectorite (e.g., INCI: pentaerythrityl tetraisostearate (and) disteardimonium hectorite (and) propylene carbonate), an activated clay (e.g., disteardimonium hectorite, stearalkonium hectorite, quaternium-18 bentonite, quaternium-18 hectorite, and benzalkonium bentonite), and a mixture thereof.

In some instances, the skin tightening compositions may include one or more additional mineral thickening agents selected from optionally modified silicas, optionally modified clays, and a mixture thereof. The additional mineral thickening agents may be selected from optionally modified silicas, optionally modified clays, and a mixture thereof. In some instance, the additional mineral thickening agents are chosen from lipophilic (organophilic) clays, in particular modified hectorites; hydrophobic-treated fumed silica; hydrophobic silica aerogels, and mixtures thereof (e.g., disteardimonium hectorite, silica silicate, or a mixture thereof).

The additional mineral thickeners may be selected from silica silylate, fumed silica, zeolite, natural clay, synthetic clay, kaolin, hectorite, organically modified hectorite (e.g., INCI: 30 pentaerythrityl tetraisostearate (and) disteardimonium hectorite (and) propylene carbonate), an activated clay (e.g., disteardimonium hectorite, stearalkonium hectorite, quaternium-18 bentonite, quaternium-18 hectorite, and benzalkonium bentonite).

i) Optionally Modified Silicas

Optionally modified silicas include fumed silica optionally subjected to a hydrophobic surface treatment, the particle size of which may be less than 1 μm. Specifically, it is possible to chemically modify the surface of the silica, by chemical reaction generating a reduced number of silanol groups present at the surface of the silica. Silanol groups can in particular be replaced by hydrophobic groups: a hydrophobic silica is then obtained. The hydrophobic groups may be:

trimethylsiloxyl groups, which are obtained especially by treating fumed silica in the presence of hexamethyldisilazane. Silicas thus treated are known as "silica silylate" according to the CTFA (6th edition, 1995). They are sold, for example, under the references Aerosil R812 by the company Degussa, and Cab-O-Sil TS-53 by the company Cabot;

dimethylsilyloxyl or polydimethylsiloxane groups, which are obtained in particular by treating fumed silica in the presence of polydimethylsiloxane or dimethyldichlorosilane. Silicas thus treated are known as "silica dimethyl silylate" according to the CTFA (6th edition, 1995). They are sold, for example, under the references Aerosil R972 and Aerosil R974 by the company Degussa, and Cab-O-Sil TS-610 and Cab-O-Sil TS-720 by the company Cabot.

The hydrophobic fumed silica in particular may have a particle size that is nanometric to micrometric, for example ranging from about 5 to 200 nm.

The optionally modified silicas may, for instance, be silica aerogel particles. Silica aerogels are porous materials obtained by replacing (by drying) the liquid component of a silica gel with air. They are generally synthesized via a sol-gel process in a liquid medium and then dried, usually by extraction with a supercritical fluid, the one most commonly used being supercritical $CO_2$. This type of drying makes it possible to avoid shrinkage of the pores and of the material. The sol-gel process and the various drying processes are described in detail in Brinker C J., and Scherer G. W., Sol-Gel Science: New York: Academic Press, 1990.

The hydrophobic silica aerogel particles may have a specific surface area per unit mass ($S_M$) ranging from 500 to 1500 m²/g, preferably from 600 to 1200 m²/g and better still from 600 to 800 m²/g, and a size expressed as the volume mean diameter (D[0.5]) ranging from 1 to 1500 μm, better still from 1 to 1000 μm, preferably from 1 to 100 μm, in particular from 1 to 30 μm, more preferably from 5 to 25 μm, better still from 5 to 20 μm, and even better still from 5 to 15 μm. In some instances, the hydrophobic silica aerogel particles have a size expressed as volume-mean diameter (D[0.5]) ranging from 1 to 30 μm, preferably from 5 to 25 μm, better still from 5 to 20 μm and even better still from 5 to 15 μm.

The hydrophobic silica aerogel particles may have a specific surface area per unit mass ($S_M$) ranging from 600 to 800 m²/g and a size expressed as the volume mean diameter (D[0.5]) ranging from 5 to 20 μm and even better still from 5 to 15 μm. The hydrophobic silica aerogel particles may have a specific surface area per unit of volume $S_V$ ranging from 5 to 60 m²/cm³, preferably from 10 to 50 m²/cm³ and better still from 15 to 40 m²/cm³.

The term "hydrophobic silica" means any silica whose surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups. In some instances, it is particularly useful to use hydrophobic silica aerogel particles surface-modified with trimethylsilyl groups. Mention may be made of the aerogels sold by the company Cabot under the references Aerogel TLD 201, Aerogel OGD 201, Aerogel TLD 203, Enova Aerogel MT 1100 and Enova Aerogel MT 1200.

ii) Optionally Modified Clays

Clays are silicates containing a cation that may be chosen from calcium, magnesium, aluminium, sodium, potassium and lithium cations, and mixtures thereof. Examples of such material include, but are not limited to clays of the smectite family, and also of the vermiculite, stevensite and chlorite families. These clays can be of natural or synthetic origin.

Mention may particularly be made of smectites, such as saponites, hectorites, montmorillonites, bentonites or beidellite and in particular synthetic hectorites (also known as laponites), such as the products sold by Rockwood Additives Limited under the names Laponite XLS, Laponite XLG, Laponite RD, Laponite RDS and Laponite XL21 (these products are sodium magnesium silicates and in particular sodium lithium magnesium silicates); bentonites, such as the product sold under the name Bentone HC by Rheox; magnesium aluminum silicates, which are in particular hydrated, such as the products sold by Vanderbilt Company under the name Veegum Ultra, Veegum HS or Veegum DGT, or also calcium silicates and in particular that in synthetic form sold by the company under the name Micro-Cel C.

In some instances organophilic clays are preferred, more particularly modified clays, such as montmorillonite, bentonite, hectorite, attapulgite and sepiolite, and mixtures thereof. The clay may be optionally modified bentonite or an optionally modified hectorite. Clays may be modified with a chemical compound chosen from quaternary amines, tertiary amines, amine acetates, imidazolines, amine soaps, fatty sulfates, alkylarylsulfonates and amine oxides, and mixtures thereof.

Mention may be made of hectorites modified with a quaternary amine, more specifically with a $C_{10}$ to $C_{22}$ fatty acid ammonium halide, such as a chloride, such as hectorite modified with distearyldimethylammonium chloride (CTFA name: Disteardimonium hectorite), for instance the product sold under the name Bentone 38V, Bentone 38V CG or Bentone EW CE by the company Elementis, or stearalkonium hectorites, such as Bentone 27 V. In some instances, the clay is preferably disteardimonium hectorite.

Mention may also be made of quaternium-18 bentonites, such as those sold under the names Bentone 34 by the company Elementis, Tixogel VP by the company United Catalyst and Claytone 40 by the company Southern Clay; stearalkonium bentonites, such as those sold under the names Tixogel LG by the company United Catalyst and Claytone AF and Claytone APA by the company Southern Clay; or quaternium-18/benzalkonium bentonites, such as that sold under the name Claytone HT by the company Southern Clay. In some instances, it is preferable that the clay is chosen from organophilic modified clays, in particular organophilic modified hectorites, in particular modified with distearyldimethylammonium chloride (CTFA name: Disteardimonium hectorite).

Non-Mineral Thickening Agents

Additional non-mineral thickening agents, if present, may be lipophilic or hydrophilic, i.e., they may be appropriate for thickening an oily phase or an anhydrous composition or they may be appropriate for thickening an aqueous phase or an aqueous composition. For anhydrous compositions, lipophilic thickening agents or thickening agents that thicken anhydrous (e.g., oily) compositions are useful. Similarly, for aqueous compositions, hydrophilic thickening agents are useful.

Non-limiting examples of the additional non-mineral thickening agents useful for thickening anhydrous compositions include $C_{12-22}$ alkyl acrylate/hydroxyethylacrylate copolymer (INTELIMER), ethylene diamine/stearyl dimer dilinoleate copolymer such as OLEOCRAFT LP-10-PA-(MV) sold by Croda, polyamide-8 such as OLEOCRAFT LP-20-PA-(MV) sold by Croda, poly $C_{10}$-$C_{30}$ alkyl acrylate such as INTELIMER IPA 13-6 or INTELIMER IPA 13-1 NG Polymer sold by Air Products & Chemicals, nylon-611/dimethicone copolymer such as Dow Corning 2-8179 Gellant sold by Dow Corning, or dextrin palmitate such as RHEOPEARL KL2-OR sold by Chiba Flour Milling.

Additional non-limiting examples of non-mineral thickening agents useful for thickening anhydrous compositions include thickening polymers such as block copolymers of styrene with isoprene, butadiene, ethylene/propylene or ethylene/butylene including those presently available under the trade name KRATON, and particularly styrene ethylene/propylene linear diblock copolymers. A related category of thickening polymer comprises polymers of alpha methylstyrene and styrene, such as those under the trade name KRISTALEX. Yet another thickening polymer comprises alkyl substituted galactomannan available under the trade name N-HANCE AG. Non-mineral thickening agents useful for thickening anhydrous compositions may also include thickening polymers such as vinyl pyrrolidone with polyethylene containing at least 25 methylene units, such as triacontanyl polyvinylpyrrolidone, under the trade name Antaron WP-660.

Non-limiting examples of additional non-mineral thickening agents may, optionally, be included for thickening aqueous compositions include xanthan gum, guar gum, biosaccharide gum, cellulose, acacia Seneca gum, sclerotium gum, agarose, pechtin, gellan gum, hyaluronic acid. Additionally, the one or more non-mineral thickening agents may be polymeric thickeners such as, for example, ammonium polyacryloyldimethyl taurate, ammonium acryloyldimethyltaurate/VP copolymer, sodium polyacrylate, acrylates copolymers, polyacrylamide, carbomer, and acrylates/C10-30 alkyl acrylate crosspolymer.

Additional, non-limiting examples of various types of non-mineral thickening agents include:

i. Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B.F. Goodrich (e.g., Carbopol® 954). In addition, other carboxylic acid polymeric agents include Ultrez® 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from carbomers, acrylates/C10-C30 alkyl acrylate crosspolymers, and mixtures thereof.

ii. Crosslinked Polyacrylate Polymers

The compositions of the present disclosure can optionally contain crosslinked polyacrylate polymers useful as thickeners or gelling agents including both cationic and nonionic polymers. Examples of useful crosslinked nonionic polyacrylate polymers and crosslinked cationic polyacrylate polymers are those described in U.S. Pat. Nos. 5,100,660, 4,849,484, 4,835,206, 4,628,078 U.S. Pat. No. 4,599,379 and EP 228,868, which are all incorporated herein by reference in their entirety.

iii. Polyacrylamide Polymers

The compositions of the present disclosure can optionally contain polyacrylamide polymers, especially nonionic polyacrylamide polymers including substituted branched or unbranched polymers. Among these polyacrylamide polymers is the nonionic polymer given the CTFA designation polyacrylamide and isoparaffin and laureth-7, available under the Tradename Sepigel 305 from Seppic Corporation. Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

The compositions may also contain thickening and texturising gels of the type as exemplified by the product range called Lubrajel® from United Guardian. These gels have moisturizing, viscosifying, stabilizing properties.

iv. Polysaccharides

A wide variety of polysaccharides can be useful herein. "Polysaccharides" refer to gelling agents that contain a backbone of repeating sugar (i.e., carbohydrate) units. Non-limiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1-3) linked glucose units with a (1-6) linked glucose every three units, a commercially available example of which is Clearogel™, provided by CS11 from Michel Mercier Products Inc.

v. Gums

Other thickening and gelling agents useful herein include materials which are primarily derived from natural sources. Non-limiting examples of these thickening and/or gelling agent include gums such as those chosen from acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, farcelluran, agar, high-methoxy pectin, low-methoxy pectin, xanthine, chitosan, starch (for example starch derived from corn, potato, wheat, rice, sweet potato and tapioca, a-starch, soluble starch), fermentation polysaccharide (for example, xanthan gum, pullulan, carciran, dextran), acidic hetero-polysaccharide derived from callus of plants belonging to *Polyantes* sp. (for example, tuberous polysaccharide), proteins (for example, sodium casein, gelatin, albumin), chondroitin sulfate, and hyaluronic acid.

Non-limiting examples of water-soluble synthetic polymers include polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, hydroxypropyl starch).

Filler(s)

The skin tightening composition includes at least one filler typically in an amount of about 1.5 to about 13 wt. %, based on the total weight of the skin tightening composition. The filler may be present in the skin tightening composition in an amount of about 1.5 to about 13 wt. %, about 2 to about 13 wt. %, about 2.5 to about 13 wt. %, about 3 to about 13 wt. %, about 3.5 to about 13 wt. %, about 4 to about 13 wt. %, about 4.5 to about 13 wt. %, about 5 to about 13 wt. %, about 6 to about 13 wt. %, about 7 to about 13 wt. %, about 8 to about 13 wt. %; about 1.5 to about 11 wt. %, about 2 to about 11 wt. %, about 2.5 to about 11 wt. %, about 3 to about 11 wt. %, about 3.5 to about 11 wt. %, about 4 to about 11 wt. %, about 4.5 to about 11 wt. %, about 5 to about 11 wt. %, about 6 to about 11 wt. %, about 7 to about 11 wt. %, about 8 to about 11 wt. %; about 1.5 to about 9 wt. %, about 2 to about 9 wt. %, about 2.5 to about 9 wt. %, about 3 to about 9 wt. %, about 3.5 to about 9 wt. %, about 4 to about 9 wt. %, about 4.5 to about 9 wt. %, about 5 to about 9 wt. %, about 6 to about 9 wt. %, about 7 to about 9 wt. %; about 1.5 to about 7 wt. %, about 2 to about 7 wt. %, about 2.5 to about 7 wt. %, about 3 to about 7 wt. %, about 3.5 to about 7 wt. %, about 4 to about 7 wt. %, about 4.5 to about 7 wt. %, or about 5 to about 7 wt. %, including all ranges and subranges thereof, based on the total weight of the skin tightening composition.

The at least one filler may be hydrophobic silica (such as, silica sylilate), nylon-12, cellulose, methacrylate crosspolymer (such as, methyl methacrylate crosspolymer), silicone powder (such as, polymethylsisesquioxane), and a combination thereof.

In some instances, the skin tightening composition preferably includes a hydrophobic silica, such as silica silylate. Hydrophobic silica are often provided in the form of particles, porous material obtained by replacing (by drying) the liquid component of a silica gel with air. They are generally synthesized via a sol-gel process in a liquid medium and then dried, usually by extraction with a supercritical fluid; the one most commonly used being supercritical $CO_2$. This type of drying makes it possible to avoid shrinkage of the pores and of the material. In some cases, the particles dissolve when combined with solvents.

The term "hydrophobic silica" means any silica whose surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups. As regards the preparation of hydrophobic silica aerogel particles modified at the surface by silylation, reference may be made U.S. Pat. No. 7,470,725, incorporated herein by reference in its entirety. In some cases, useful hydrophobic silica particles are surface-modified with trimethylsilyl groups. In at least one instance, the hydrophobic silica is aerogel.

Hydrophobic silica include those that exhibit a specific surface area per unit of mass (SM) ranging from 500 to 1500 $m^2/g$, from 600 to 1200 $m^2/g$, or 600 to 800 $m^2/g$, and a size, expressed as the volume-mean diameter (D[0.5]), ranging from 1 to 1500 μm, from 1 to 1000 μm, or from 1 to 100 μm, in particular from 1 to 30 μm, from 5 to 25 μm, or from 5 to 20 μm, and in some cases from 5 to 15 μm. In some cases, the hydrophobic silica particles used in the skin tightening composition have a size, expressed as the volume-mean diameter (D[0.5]), ranging from 1 to 30 μm, from 5 to 25 μm, from 5 to 20 μm or from 5 to 15 μm. In some instances, the hydrophobic silica particles have a specific surface area per unit of mass (SM) ranging from 600 to 800 $m^2/g$ and a size expressed as the volume-mean diameter (D[0.5]) ranging from 5 to 20 μm or from 5 to 15 μm.

The specific surface area per unit of mass can be determined by the nitrogen absorption method, known as the BET (Brunauer-Emmett-Teller) method, described in The Journal of the American Chemical Society, Vol. 60, page 309, February 1938 and corresponding to the international standard ISO 5794/1 (appendix D). The BET specific surface area corresponds to the total specific surface area of the particles under consideration.

The sizes of hydrophobic silica particles (e.g., aerogel particles) can be measured by static light scattering using a commercial particle size analyzer of MasterSizer 2000 type from Malvern. The data are processed on the basis of the Mie scattering theory. This theory, which is exact for isotropic particles, makes it possible to determine, in the case of non-spherical particles, an "effective" particle diameter. This theory is described in particular in the publication by Van de Hulst, H. C., "Light Scattering by Small Particles", Chapters 9 and 10, Wiley, New York, 1957.

The hydrophobic silica particles may advantageously have a tapped density p ranging from 0.02 $g/cm^3$ to 0.10 $g/cm^3$, from 0.03 $g/cm^3$ to 0.10 $g/cm^3$, from 0.04 $g/cm^3$ to 0.10 $g/cm^3$, or from 0.05 $g/cm^3$ to 0.08 $g/cm^3$. The density p, known as the tapped density, may be assessed according to the following protocol: 40 g of powder are poured into a measuring cylinder; the measuring cylinder is then placed on a Stay 2003 machine from Stampf Volumeter; the measuring cylinder is then subjected to a series of 2500 packing motions (this operation is repeated until the difference in volume between two consecutive tests is less than 2 percent); the final volume Vf of packed powder is then measured directly on the measuring cylinder. The tapped density is determined by the ratio w/Vf, in this instance 40/Vf (Vf being expressed in $cm^3$ and win g).

In some cases, the hydrophobic silica particles (e.g., aerogel particles) may have a specific surface area per unit of volume SV ranging from 5 to 100 $m^2/cm^3$, from 10 to 90 $m^2/cm^3$, from 15 to 40 $m^2/cm^3$, from 20 to 85 $m^2/cm^3$, or from 24 to 80 $m^2/cm^3$. The specific surface area per unit of volume is given by the relationship: $S_V = S_M \times \rho$, where ρ is the tapped density, expressed in $g/cm^3$, and $S_M$ is the specific surface area per unit of weight, expressed in $m^2/g$, as defined above.

The hydrophobic silica particles may have an oil-absorbing capacity, measured at the wet point, ranging from 5 to 18 ml/g, from 6 to 15 ml/g, or from 8 to 12 ml/g. The absorption capacity measured at the wet point, denoted Wp, corresponds to the amount of oil which is necessary to add to 100 g of particles in order to obtain a homogeneous paste. It is measured according to the "wet point" method or method of determination of oil uptake of a powder described in the standard NF T 30-022.

Mention may be made of hydrophobic silica sold under the name VM-2260 (INCI name: Silica silylate) by Dow Corning, the particles of which have a mean size of approximately 1000 microns and a specific surface area per unit of mass ranging from 600 to 800 $m^2/g$. Mention may also be made of the aerogels sold by Cabot under the references Aerogel TLD 201, Aerogel OGD 201, Aerogel TLD 203, Enova® Aerogel MT 1100 and Enova Aerogel MT 1200. Additionally, the hydrophobic silica aerogel particles sold under the name VM-2270 (INCI name: Silica silylate), by the company Dow Corning, the particles having an average size ranging from 5-15 microns and a specific surface area per unit of mass ranging from 600 to 800 $m^2/g$ may be useful.

Film Former(s)

The skin tightening composition includes at least one film former, which is preferably hydrophobic, typically in an amount of about 5 to about 45 wt. %, based on the total weight of the skin tightening composition. The film former may be present in the skin tightening composition in an amount of about 5 to about 45 wt. %, about 6 to about 45 wt. %, about 8 to about 45 wt. %, about 10 to about 45 wt. %, about 12 to about 45 wt. %; about 5 to about 45 wt. %; about 5 to about 40 wt. %, about 6 to about 40 wt. %, about 8 to about 40 wt. %, about 10 to about 40 wt. %, about 12 to about 40 wt. %; about 5 to about 35 wt. %, about 6 to about 35 wt. %, about 8 to about 35 wt. %, about 10 to about 35 wt. %, about 12 to about 35 wt. %; about 5 to about 35 wt. %; about 5 to about 30 wt. %, about 6 to about 30 wt. %, about 8 to about 30 wt. %, about 10 to about 30 wt. %, about 12 to about 30 wt. %; about 5 to about 25 wt. %, about 6 to about 25 wt. %, about 8 to about 25 wt. %, about 10 to about 25 wt. %, about 12 to about 25 wt. %; about 5 to about 20 wt. %, about 6 to about 20 wt. %, about 8 to about 20 wt. %, about 10 to about 20 wt. %, about 12 to about 20 wt. %; about 5 to about 18 wt. %, about 6 to about 18 wt. %, about 8 to about 18 wt. %, about 10 to about 18 wt. %, about 12 to about 18 wt. %, about 5 to about 16 wt. %, about 6 to about 16 wt. %, about 8 to about 16 wt. %, about 10 to about 16 wt. %, about 12 to about 16 wt. %, about 5 to about 14 wt. %, about 6 to about 14 wt. %, about 8 to about 14 wt. %, about 10 to about 14 wt. %, about 12 to about 14 wt. %, including all ranges and subranges thereof, based on the total weight of the skin tightening composition.

The term film formers are typically compounds capable of forming, by themselves or in the presence of an auxiliary film-forming agent, a macroscopically continuous deposit on a support, especially on keratin materials, and preferably a cohesive deposit, and better still a deposit whose cohesion and mechanical properties are such that said deposit may be isolable and manipulable in isolation, for example when said deposit is prepared by pouring onto a non-stick surface, for instance a Teflon-coated or silicone-coated surface.

The at least one film former may be chosen from acrylic acid/isobutyl acrylates/isobornyl acrylate copolymer, trimethylsiloxysilicate, acrylates/isobornyl acrylate copolymer, norbornene/tris(trimethylsiloxy)silylnorbornene copolymer, acrylate/polytrimethyl siloxymethacrylate copolymer, acrylates/polymethylsiloxymethacrylate copolymer, C30-45 alkyldimethylsilylpolypropylsilsequixane, trimethylsilsesquixane, polypropylsilsesquixane, acrylates/dimethicone copolymer, octylacrylamide/acrylates/butylaminoethyl methacrylate copolymer, VA/butyl maleate/isobornyl acrylate copolymer, acrylates/t-butylacrylamide copolymer, polyvinylpyrrolidone/vinyl acetate copolymer, triacontanyl PVP copolymer, acrylates/dimethylaminoethyl methacrylate copolymer, and a combination thereof. In some cases, the at least one film former includes one or more of acrylic acid/isobutyl acrylates/isobornyl acrylate copolymer, trimethylsiloxysilicate, acrylates/isobornyl acrylate copolymer, norbornene/tris(trimethylsiloxy)silylnorbornene copolymer, acrylates/polymethylsiloxymethacrylate copolymer, and a combination thereof.

The film former may be a hydrophobic film-forming polymer. The term "hydrophobic film-forming polymer" denotes a film-forming polymer that has no or limited affinity for water and, in this respect, does not lend itself to a formulation in the form of a solute in an aqueous medium. In particular, the term "hydrophobic polymer" means a polymer having a solubility in water at 25° C. of less than 1% by weight.

The film formers may be chosen from the following and, optionally hydrophobic:
film-forming polymers that are soluble in an organic solvent medium, in particular liposoluble polymers; this means that the polymer is soluble or miscible in the organic medium and forms a single homogeneous phase when it is incorporated into the medium; and
film-forming polymers that are dispersible in an organic solvent medium, which means that the polymer forms an insoluble phase in the organic medium, the polymer remaining stable and/or compatible once incorporated into this medium. In particular, such polymers may be in the form of non-aqueous dispersions of polymer particles, preferably dispersions in silicone oils or hydrocarbon-based oils; in one embodiment, the non-aqueous polymer dispersions comprise polymer particles stabilized on their surface with at least one stabilizer; these non-aqueous dispersions are often referred to as NADs.

Hydrophobic film-forming polymers that may be mentioned include homopolymers and copolymers of a compound bearing an ethylenic unit, acrylic polymers and copolymers, polyurethanes, polyesters, silicone polymers such as polymers bearing a non-silicone organic backbone grafted with monomers containing a polysiloxane, and polyisoprenes.

In some instances, useful hydrophobic film-forming polymers include lipodispersible film-forming polymers in the form of non-aqueous dispersions of polymer particles, block ethylenic copolymers, vinyl polymers comprising at least one carbosiloxane dendrimer-based unit, silicone acrylate copolymers and mixtures thereof, preferably lipodispersible film-forming polymers in the form of non-aqueous dispersions of polymer particles (NADs).

i. Lipodispersible Film-Forming Polymers in the Form of Non-Aqueous Dispersions of Polymer Particles, Also Known as NADs Non-aqueous dispersions of hydrophobic film-forming polymer that may be used include dispersions of particles of a grafted ethylenic polymer, preferably an acrylic polymer, in a liquid oily phase for example, in the form of surface-stabilized particles dispersed in the liquid fatty phase. The dispersion of surface-stabilized polymer particles may be manufactured as described in document WO 04/055081, which is incorporated herein by reference in its entirety.

ii. Block Ethylenic Copolymer

The film former may be a block ethylenic copolymer, containing at least a first block with a glass transition temperature ($T_g$) of greater than or equal to 40° C. and being totally or partly derived from one or more first monomers, which are such that the homopolymer prepared from these monomers has a glass transition temperature of greater than or equal to 40° C., and at least a second block with a glass transition temperature of less than or equal to 20° C. and being derived totally or partly from one or more second monomers, which are such that the homopolymer prepared from these monomers has a glass transition temperature of less than or equal to 20° C., said first block and said second block being connected together via a statistical intermediate segment comprising at least one of said first constituent monomers of the first block and at least one of said second constituent monomers of the second block, and said block copolymer having a polydispersity index I of greater than 2. Polymers of this type that are suitable for use in the invention are described in document EP 1 411 069, which is incorporated herein by reference in its entirety. A non-limiting examples includes the product MEXOMER PAS (acrylic acid/isobutyl acrylate/isobornyl acrylate copolymer diluted to 50% in isododecane) sold by the company Chimex.

iii. Vinyl Polymer Comprising at Least one Carbosiloxane Dendrimer-Based Unit

The hydrophobic film-forming polymer may be at least one vinyl polymer comprising at least one carbosiloxane dendrimer-based unit. The vinyl polymer typically has a backbone and at least one side chain, which comprises a carbosiloxane dendrimer-based unit having a carbosiloxane dendrimer structure. Vinyl polymers comprising at least one carbosiloxane dendrimer unit as described in applications WO 03/045 337 and EP 963 751, which are incorporated herein by reference in their entirety.

The term "carbosiloxane dendrimer structure" is a molecular structure with branched groups of high molecular masses, said structure having high regularity in the radial direction starting from the bond to the backbone. Such carbosiloxane dendrimer structures are described in the form of a highly branched siloxane-silylalkylene copolymer in the laid-open Japanese patent application Kokai 9-171 154, which is incorporated herein by reference in their entirety.

A vinyl polymer bearing at least one carbosiloxane dendrimer-based unit has a molecular side chain containing a carbosiloxane dendrimer structure, and may be derived from the polymerization of:

(A) from 0 to 99.9 parts by weight of a vinyl monomer; and (B) from 100 to 0.1 part by weight of a carbosiloxane dendrimer containing a radical-polymerizable organic group, represented by the general formula:

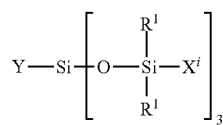

in which Y represents a radical-polymerizable organic group, $R^1$ represents an aryl group or an alkyl group containing from 1 to 10 carbon atoms, and $X^i$ represents a silylalkyl group which, when i=1, is represented by the formula:

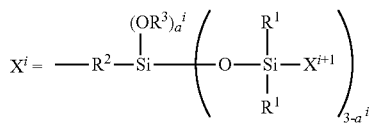

in which $R^1$ is as defined above, $R^2$ represents an alkylene group containing from 2 to 10 carbon atoms, $R^3$ represents an alkyl group containing from 1 to 10 carbon atoms, $X^{i+1}$ represents a hydrogen atom, an alkyl group containing from 1 to 10 carbon atoms, an aryl group, or the silylalkyl group defined above with i=i+1; i is an integer from 1 to 10 which represents the generation of said silylalkyl group, and a' is an integer from 0 to 3;

in which said radical-polymerizable organic group contained in the component (A) is chosen from:

organic groups containing a methacrylic group or an acrylic group and that are represented by the formulae:

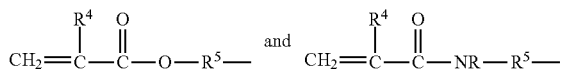

in which $R^4$ represents a hydrogen atom or an alkyl group, $R^5$ represents an alkylene group containing from 1 to 10 carbon atoms; and organic groups containing a styryl group and that are represented by the formula:

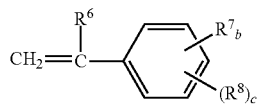

in which $R^6$ represents a hydrogen atom or an alkyl group, $R^7$ represents an alkyl group containing from 1 to 10 carbon atoms, $R^8$ represents an alkylene group containing from 1 to 10 carbon atoms, b is an integer from 0 to 4, and c is 0 or 1, such that if c is 0, $-(R^8)_c-$ represents a bond.

The monomer of vinyl type that is the component (A) in the vinyl polymer is a monomer of vinyl type that contains a radical-polymerizable vinyl group.

The following are examples of this monomer of vinyl type: methyl methacrylate, ethyl methacrylate, n-propyl methacrylate, isopropyl methacrylate or a methacrylate of an analogous lower alkyl; glycidyl methacrylate; butyl methacrylate, butyl acrylate, n-butyl methacrylate, isobutyl methacrylate, tert-butyl acrylate, tert-butyl methacrylate, n-hexyl methacrylate, cyclohexyl methacrylate, 2-ethylhexyl acrylate, 2-ethylhexyl methacrylate, octyl methacrylate, lauryl methacrylate, stearyl acrylate, stearyl methacrylate or a higher-analogue methacrylate; vinyl acetate, vinyl propionate or a vinyl ester of an analogous lower fatty acid; vinyl caproate, vinyl 2-ethylhexoate, vinyl laurate, vinyl stearate or an ester of an analogous higher fatty acid; styrene, vinyltoluene, benzyl methacrylate, phenoxyethyl methacrylate, vinylpyrrolidone or similar vinylaromatic monomers; methacrylamide, N-methylolmethacrylamide, N-methoxymethyl-methacrylamide, isobutoxymethoxymethacrylamide, N,N-dimethylmethacrylamide or similar monomers of vinyl type containing amide groups; hydroxyethyl methacrylate, hydroxypropyl alcohol methacrylate or similar monomers of vinyl type containing hydroxyl groups; acrylic acid, methacrylic acid, itaconic acid, crotonic acid, fumaric acid, maleic acid or similar monomers of vinyl type containing a carboxylic acid group; tetrahydrofurfuryl methacrylate, butoxyethyl methacrylate, ethoxydiethylene glycol methacrylate, polyethylene glycol methacrylate, polypropylene glycol monomethacrylate, hydroxybutyl vinyl ether, cetyl vinyl ether, 2-ethylhexyl vinyl ether or a similar monomer of vinyl type with ether bonds; methacryloxypropyltrimethoxysilane, polydimethylsiloxane containing a methacrylic group on one of its molecular ends, polydimethylsiloxane containing a styryl group on one of its molecular ends, or a similar silicone compound containing unsaturated groups; butadiene; vinyl chloride; vinylidene chloride; methacrylonitrile; dibutyl fumarate; anhydrous maleic acid; anhydrous succinic acid; methacryl glycidyl ether; an organic salt of an amine, an ammonium salt, and an alkali metal salt of methacrylic acid, of itaconic acid, of crotonic acid, of maleic acid or of fumaric acid; a radical-polymerizable unsaturated monomer containing a sulfonic acid group such as a styrenesulfonic acid group; a quaternary ammonium salt derived from methacrylic acid, such as 2-hydroxy-3-methacryloxypropyltrimethylammonium chloride; and a methacrylic acid ester of an alcohol containing a tertiary amine group, such as a methacrylic acid ester of diethylamine.

Multifunctional monomers of vinyl type may, optionally, be included in certain cases. The following are examples of such compounds: trimethylolpropane tri methacrylate, pentaerythrityl tri methacrylate, ethylene glycol di methacrylate, tetraethylene glycol dimethacrylate, polyethylene glycol dimethacrylate, 1,4-butanediol dimethacrylate, 1,6-hexanediol dimethacrylate, neopentyl glycol dimethacrylate, trimethylolpropane trioxyethylmethacrylate, tris(2-hydroxyethyl) isocyanurate di methacrylate, tris (2-hydroxyethyl) isocyanurate tri methacrylate, polydimethylsiloxane capped with styryl groups bearing divinylbenzene groups on the two ends, or similar silicone compounds bearing unsaturated groups.

The number-average molecular mass of the vinyl polymer bearing a carbosiloxane dendrimer may be chosen within the range between 3,000 g/mol and 2,000,000 g/mol and preferably between 5,000 g/mol and 800,000 g/mol. It may be a liquid, a gum, a paste, a solid, a powder, or any other form. The preferred forms are solutions consisting of the dilution of a dispersion or of a powder in solvents such as a silicone oil or an organic oil.

According to one embodiment, a vinyl polymer grafted in the sense of the present disclosure may be conveyed in an oil or a mixture of oils, which is/are preferably volatile, chosen in particular from silicone oils and hydrocarbon-based oils, and mixtures thereof. A non-limiting silicone oil that may, optionally be used is cyclopentasiloxane. Similarly, a non-limiting hydrocarbon-based oil that is may be used is isododecane.

Vinyl polymers grafted with at least one carbosiloxane dendrimer-based unit include the polymers sold under the names TIB 4-100, TIB 4-101, TIB 4-120, TIB 4-130, TIB 4-200, FA 4002 ID (TIB 4-202), TIB 4-220 and FA 4001 CM (TIB 4-230) by the company Dow Corning.

In some instances, the vinyl polymer grafted with at least one carbosiloxane dendrimer-based unit is an acrylate/polytrimethyl siloxymethacrylate copolymer, for example, the product sold in isododecane under the name Dow Corning FA 4002 ID Silicone Acrylate.

iv. Silicone Acrylate Copolymers

In some instances, one or more of the film formers include at least one copolymer comprising carboxylate groups and polydimethylsiloxane groups. The term "copolymer comprising carboxylate groups and polydimethylsiloxane groups" means a copolymer obtained from (a) one or more carboxylic (acid or ester) monomers, and (b) one or more polydimethylsiloxane (PDMS) chains. The term "carboxylic monomer" means both carboxylic acid monomers and carboxylic acid ester monomers.

The monomer (a) may be chosen, for example, from acrylic acid, methacrylic acid, maleic acid, fumaric acid, itaconic acid, crotonic acid, esters thereof and mixtures of these monomers. Esters that may be mentioned include the following monomers: acrylate, methacrylate, maleate, fumarate, itaconate and/or crotonate. According to at least one embodiment of the invention, the monomers in ester form are more particularly chosen from linear or branched, preferably $C_1$-$C_{24}$ and better still $C_1$-$C_{22}$ alkyl acrylates and methacrylates, the alkyl radical preferably being chosen from methyl, ethyl, stearyl, butyl and 2-ethylhexyl radicals, and mixtures thereof. Thus, in some instances, the copolymer comprises as carboxylate groups at least one group chosen from acrylic acid and methacrylic acid, and methyl, ethyl, stearyl, butyl or 2-ethylhexyl acrylate or methacrylate, and mixtures thereof.

The term "polydimethylsiloxanes" (also known as organopolysiloxanes and abbreviated as PDMS) denotes any organosilicon polymer or oligomer of linear structure, of variable molecular weight, obtained by polymerization and/or polycondensation of suitably functionalized silanes, and consisting essentially of a repetition of main units in which the silicon atoms are linked together via oxygen atoms (siloxane bond ≡Si—O—Si≡), comprising trimethyl radicals directly linked via a carbon atom to said silicon atoms. The PDMS chains that may be used to obtain the copolymer may comprise at least one polymerizable radical group, preferably located on at least one of the ends of the chain, i.e. the PDMS may contain, for example, a polymerizable radical group on the two ends of the chain or one polymerizable radical group on one end of the chain and one trimethylsilyl end group on the other end of the chain. The polymerizable radical group may especially be an acrylic or methacrylic group, in particular a group $CH_2=CR_1-CO-O-R_2$, in which $R_1$ represents a hydrogen or a methyl group and $R_2$ represents —$CH_2$—, —$(CH_2)_n$— with n=3, 5, 8 or 10, —$CH_2$—$CH(CH_3)$—$CH_2$—, —$CH_2$—$CH_2$—O—$CH_2$—$CH_2$—, —$CH_2$—$CH_2$—O—$CH_2$—$CH_2$—$CH(CH_3)$—$CH_2$—, —$CH_2$—$CH_2$—O—$CH_2$—, or —$CH_2$—O—$CH_2$—$CH_2$—$CH_2$—.

The copolymers are generally obtained according to the usual methods of polymerization and grafting, for example by free-radical polymerization (A) of a PDMS comprising at least one polymerizable radical group (for example on one of the ends of the chain or on both ends) and (B) of at least one carboxylic monomer. The copolymers obtained may have a molecular weight ranging from about 3,000 g/mol to 200,000 g/mol and preferably from about 5,000 g/mol to 100,000 g/mol. The copolymer may be in its native form or in dispersed form in a solvent such as lower alcohols containing from 2 to 8 carbon atoms, for instance isopropyl alcohol, or oils, for instance volatile silicone oils (for example, cyclopentasiloxane).

Additional copolymers that mention may be made include copolymers of acrylic acid and of stearyl acrylate containing polydimethylsiloxane grafts, copolymers of stearyl methacrylate containing polydimethylsiloxane grafts, copolymers of acrylic acid and of stearyl methacrylate containing polydimethylsiloxane grafts, copolymers of methyl methacrylate, butyl methacrylate, 2-ethylhexyl acrylate and stearyl methacrylate containing polydimethylsiloxane grafts. Mention may also be made in particular of the copolymers sold by the company Shin-Etsu under the names KP-561 (CTFA name: acrylates/dimethicone), KP-541 in which the copolymer is dispersed at 60% by weight in isopropyl alcohol (CTFA name: acrylates/dimethicone and isopropyl alcohol), and KP-545 in which the copolymer is dispersed at 30% in cyclopentasiloxane (CTFA name: acrylates/dimethicone and cyclopentasiloxane). Mention may also be made of the grafted copolymer of polyacrylic acid and dimethylpolysiloxane dissolved in isododecane, sold by the company Shin-Etsu under the name KP-550.

v. Adhesive Polymer

The skin tightening composition may include one or more film formers that are adhesive polymers. In various embodiments, the at least one adhesive polymer may be amorphous, crystalline, or semicrystalline. In some instances, the adhesive polymer may have a $T_g$ greater than about 25° C., such as greater than about 50° C., greater than about 75° C., or greater than about 100° C., according to various embodiments. In further instances, the adhesive polymer may have a $T_g$ less than about 25° C., such as less than about 0° C., less than about −25° C., or less than about −50° C.

As non-limiting examples of adhesive polymers having a $T_g$ greater than about 25° C. may be mentioned polymer particles of $C_1$-$C_4$ alkyl(methacrylate)polymer, stabilized in a non-aqueous dispersion, referred to herein for ease of reference as an "oil dispersion," such as those described in WO2015/091513 which is incorporated by reference herein. By way of example, the $C_1$-$C_4$ alkyl (meth)acrylate monomers may be chosen from methyl (meth)acrylate, ethyl (meth)acrylate, n-propyl (meth)acrylate, isopropyl (meth) acrylate, n-butyl (meth)acrylate and tert-butyl (meth)acrylate. For example, the polymer may be a methyl acrylate and/or ethyl acrylate polymer.

The polymer may also comprise an ethylenically unsaturated acid monomer or the anhydride thereof, chosen especially from ethylenically unsaturated acid monomers comprising at least one carboxylic, phosphoric or sulfonic acid function, such as crotonic acid, itaconic acid, fumaric acid, maleic acid, maleic anhydride, styrenesulfonic acid, vinylbenzoic acid, vinylphosphoric acid, acrylic acid, methacrylic acid, acrylamidopropanesulfonic acid or acrylamidoglycolic acid, and salts thereof. For example, the ethylenically unsaturated acid monomer may be chosen from (meth) acrylic acid, maleic acid, and maleic anhydride.

Volatile Hydrocarbon(s)

The term "volatile hydrocarbon" is a hydrocarbon that is volatile at ambient temperature (25° C.) and normal pressure (1 atm) and may include, for example, isododecane, isohexadecane. The volatile hydrocarbons may be in the form of an oil. The term "oil" is understood to mean a compound which is liquid at ambient temperature (25° C.) and normal pressure (1 atm), and which, when it is introduced in a proportion of at least 1% by weight into water at 25° C. is not soluble in water or soluble to a level of less than 10% by weight, with respect to the weight of oil introduced into the water. The term "hydrocarbon oil" is oil comprising hydrogen and carbon atoms, and containing no silicon atoms.

Suitable volatile hydrocarbons include, but are not limited to, those having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of ISOPAR or PERMETHYL, the $C_8$ to $C_{16}$ branched esters such as isohexyl or isodecyl neopentanoate and their mixtures. Preferably, the volatile hydrocarbon oils have a flash point of below 40° C.

In some instances, the skin tightening composition includes at least one volatile hydrocarbon chosen from isoparaffin, isohexadecane, isododecane, isodecane, undecane, tridecane, dodecane, isohexyl, isodecyl, neopentanoate, or a combination thereof. In at least one instance, isododecane and/or isoparaffins (e.g., $C_{8-9}$ isoparaffin) are preferred. The skin tightening composition may be formulated to include volatile hydrocarbons that contain no silicon atoms.

The total amount of the volatile hydrocarbon may vary but is typically about 20 to about 85 wt. %, based on the total weight of the skin tightening composition. In some cases, the total amount of volatile hydrocarbons is about 20 to about 80 wt. %, about 20 to about 75 wt. %; about 25 to about 85 wt. %, about 25 to about 80 wt. %, about 25 to about 75 wt. %; about 32 to about 85 wt. %, about 32 to about 80 wt. %, about 32 to about 75 wt. %; about 35 to about 85 wt. %, about 35 to about 80 wt. %, about 35 to about 75 wt. %; about 40 to about 85 wt. %, about 40 to about 80 wt. %, about 40 to about 75 wt. %; about 45 to about 85 wt. %, about 45 to about 80 wt. %, about 45 to about 75 wt. %; about 50 to about 85 wt. %, about 50 to about 80 wt. %, about 50 to about 75 wt. %; about 55 to about 85 wt. %, about 55 to about 80 wt. %, about 55 to about 75 wt. %; about 60 to about 85 wt. %, about 60 to about 80 wt. %, about 60 to about 75 wt. %; about 65 to about 85 wt. %, about 65 to about 80 wt. %, or about 65 to about 75 wt. %, including ranges and subranges thereof, based on the total weight of the skin tightening composition.

The skin tightening composition may include a lower amount of volatile hydrocarbon oils (for example, when the skin tightening composition is an emulsion). For example, the amount of volatile hydrocarbon present in the skin tightening composition may be from about 20 to about 70 wt. %, about 25 to about 70 wt. %, about 30 to about 70 wt. %, about 35 to about 70 wt. %, about 40 to about 70 wt. %, about 45 to about 70 wt. %, about 50 to about 70 wt. %, about 55 to about 70 wt. %; about 20 to about 60 wt. %, about 25 to about 60 wt. %, about 30 to about 60 wt. %, about 35 to about 60 wt. %, about 40 to about 60 wt. %, about 45 to about 60 wt. %, about 50 to about 60 wt. %; about 20 to about 55 wt. %, about 25 to about 55 wt. %, about 30 to about 55 wt. %, about 35 to about 55 wt. %, about 40 to about 55 wt. %, about 45 to about 55 wt. %, about 50 to about 55 wt. %; about 20 to about 50 wt. %, about 25 to about 50 wt. %, about 30 to about 50 wt. %, about 35 to about 50 wt. %, about 40 to about 50 wt. %, or about 45 to about 50 wt. %, including ranges and subranges thereof, based on the total weight of the skin tightening composition.

Non-Ionic Surfactant(s)

The skin tightening composition may, optionally, include one or more nonionic surfactants. Although the skin tightening composition is typically an emulsion when containing one or more nonionic surfactants, the skin tightening composition may alternatively be anhydrous when containing such nonionic surfactants.

The nonionic surfactant(s) may include one or more of peg-30 di polyhydroxystearate, polyglyceryl-4 diisostearate/polyhydroxystearate/sebacate, polyglyceryl-4 isostearate, polyglyceryl-2 dipolyhydroxystearate, dimethicone (and) peg/ppg-18/18 dimethicone, lauryl peg-9 polydimethylsiloxyethyl dimethicone, and a combination thereof. The nonionic surfactant can be, for example, selected from alcohols, alpha-diols, alkylphenols and esters of fatty acids, these compounds being ethoxylated, propoxylated or glycerolated and having at least one fatty chain comprising, for example, from 8 to 18 carbon atoms. The number of ethylene oxide or propylene oxide groups of the foregoing compounds may range from 2 to 50, and the number of glycerol groups may range from 1 to 30. Mention may be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol (C6-C24)alkylpolyglycosides; N—(C6-C24)alkylglucamine derivatives, amine oxides such as (C10-C14)alkylamine oxides or N—(C10-C14)acylaminopropylmorpholine oxides; and mixtures thereof. Maltose derivatives may also be mentioned.

The nonionic surfactants may be chosen from polyoxyalkylenated or polyglycerolated nonionic surfactants. The oxyalkylene units are more preferably oxyethylene or oxypropylene units, or a combination thereof, and are preferably oxyethylene units.

In some cases, the nonionic surfactant may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and mixtures thereof.

Examples of ethoxylated fatty esters that may be mentioned include the adducts of ethylene oxide with esters of lauric acid, palmitic acid, stearic acid or behenic acid, and mixtures thereof, especially those containing from 9 to 100 oxyethylene groups—such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof. As glyceryl esters of fatty acids, glyceryl stearate (glyceryl mono-, di- and/or tristearate) (CTFA name: glyceryl stearate) or glyceryl ricinoleate and mixtures thereof can in particular be cited. As glyceryl esters of $C_8$-$C_{24}$ alkoxylated fatty acids, polyethoxylated glyceryl stearate (glyceryl mono-, di- and/or tristearate) such as PEG-20 glyceryl stearate can for example be cited. Mixtures of these surfactants, such as for example the product containing glyceryl stearate and PEG-100 stearate, marketed under the name ARLACEL 165 by Uniqema, and the product containing glyceryl stearate (glyceryl mono- and distearate) and potassium stearate marketed under the name TEG1 N by Goldschmidt (CTFA name: glyceryl stearate SE), can also be used.

Typically, the amount of nonionic surfactants included in the skin tightening compositions, when present, ranges from about 0.5 to about 10 wt. %, about 0.5 to about 8 wt. %, about 0.5 to about 6 wt. %, about 0.5 to about 5 wt. %, about 0.5 to about 4 wt. %; about 1 to about 10 wt. %, about 1 to about 8 wt. %, about 1 to about 6 wt. %, about 1 to about 5 wt. %, about 1 to about 4 wt. %; about 2 to about 10 wt. %, about 2 to about 8 wt. %, about 2 to about 6 wt. %, about 2 to about 5 wt. %, about 2 to about 4 wt. %; about 3 to about 10 wt. %, about 3 to about 8 wt. %, about 3 to about 6 wt. %, about 3 to about 5 wt. %, about 3 to about 4 wt. %, including all ranges and subranges thereof, based on the total weight of the skin tightening composition.

Dispersant(s)

The skin tightening composition may, optionally, include one or more dispersant. The dispersant may be chosen from olyoxyethylene glycol ethers or esters (POE/PEG ethers or esters) or polyoxypropylene glycol ethers or esters (PPG ethers or esters), from sugar ethers or esters, from glycerol or polyglycerol ethers or esters and from ethoxylated glyceride esters (POE glyceryl esters), polyhydroxystearic acid, or a combination thereof.

The dispersant may be selected such that it protects various ingredients of the skin tightening composition, such as coloring particles, that are solid at room temperature and atmospheric pressure against their aggregation or flocculation when it is placed in contact with an aqueous composition. More generally, the dispersant may be a surfactant, an oligomer, a polymer or a mixture of several thereof, bearing one or more functionalities that have strong affinity for the surface of the compounds to be dispersed. In some instances, the dispersant may be physically adsorbed onto the surface of the particles to be dispersed.

As dispersants that are suitable for use in the invention, mention may be made especially of surfactants with high hydrophilicity, with an HLB of greater than 10, preferably greater than 13 and more particularly greater than 15. The term "HLB of greater than or equal to 10" means a surfactant having, at 25° C., an HLB balance (hydrophilic-lipophilic balance), within the Griffin meaning, of greater than or equal to 10.

The dispersant may be nonionic and/or chosen from polyoxyethylene glycol ethers or esters (POE/PEG ethers or esters) or polyoxypropylene glycol ethers or esters (PPG ethers or esters), from sugar ethers or esters, from glycerol or polyglycerol ethers or esters and from ethoxylated glyceride esters (POE glyceryl esters) or from mixtures thereof.

In some instance, the skin tightening composition may be formulated such that the amount of dispersants and amount of coloring particles that are solid at room temperature and atmospheric pressure may be present in an amount of 0.1% to 20% by weight, preferably from 0.5% to 10% by weight and better still from 1% to 7% by weight, or even from 2% to 5% by weight of dispersant(s), relative to the total weight of the said particles.

Typically, the amount of dispersants included in the skin tightening compositions, when present, ranges from about 0.5 to about 10 wt. %, about 0.5 to about 8 wt. %, about 0.5 to about 6 wt. %, about 0.5 to about 5 wt. %, about 0.5 to about 4 wt. %; about 1 to about 10 wt. %, about 1 to about 8 wt. %, about 1 to about 6 wt. %, about 1 to about 5 wt. %, about 1 to about 4 wt. %; about 1.5 to about 10 wt. %, about 1.5 to about 8 wt. %, about 1.5 to about 6 wt. %, about 1.5 to about 5 wt. %, about 1.5 to about 4 wt. %, including all ranges and subranges thereof, based on the total weight of the skin tightening composition.

Water

The skin tightening composition may, optionally, include water. The amount of water present in the skin tightening composition, when present, may range from about 5 to about 60 wt. %, about 10 to about 60 wt. %, about 15 to about 60 wt. %; about 5 to about 50 wt. %, about 10 to about 50 wt. %, about 15 to about 50 wt. %; about 5 to about 40 wt. %, about 10 to about 40 wt. %, about 15 to about 40 wt. %; about 5 to about 35 wt. %, about 10 to about 35 wt. %, about 15 to about 35 wt. %; about 5 to about 30 wt. %, about 10 to about 30 wt. %, about 15 to about 30 wt. %; about 5 to about 25 wt. %, about 10 to about 25 wt. %, about 15 to about 25 wt. %, including ranges and subranges thereof, based on the total weight of the skin tightening composition. In at least one instance, the amount of water in the skin tightening composition is about 20 wt. %, based on the total weight of the skin tightening composition. As noted above, in some instances, the skin tightening composition is anhydrous.

Water-Soluble Solvents

The skin tightening composition may optionally include one or more water-soluble solvents. The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water soluble solvent has a solubility of at least 60%, 70%, 80%, or 90%. Non-limiting examples of water-soluble solvents include, for example, glycerin, $C_{1-4}$ alcohols, organic solvents, fatty alcohols, fatty ethers, fatty esters, polyols, glycols, and any a mixture thereof. In some instances, the skin tightening composition includes one or more $C_{1-4}$ alcohols, for example, ethanol.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

The total amount of the water-soluble solvents in the skin tightening composition, if present, may vary but is typically about 0.01 to about 25 wt. %, based on the total weight of the skin tightening composition. In some cases, the total amount of water-soluble solvents is about 0.01 to about 20 wt. %, about 0.01 to about 15 wt. %, about 0.01 to about 10 wt. %, about 0.1 to about 25 wt. %, about 0.1 to about 20 wt. %, about 0.1 to about 15 wt. %, about 0.1 to about 10 wt. %, about 1 to about 25 wt. %, about 1 to about 20 wt. %, about 1 to about 15 wt. %, about 1 to about 10 wt. %, or about 1 to about 8 wt. %, including all ranges and subranges thereof, based on the total weight of the skin tightening composition.

Inorganic Pigments

The skin tightening compositions may optionally include one or more inorganic pigments. Non-limiting examples include titanium dioxide, zirconium oxide, cerium oxide, zinc oxide, iron oxide, mica, alumina, aluminum hydroxide, chromium oxide, manganese violet, ultramarine blue, chromium hydrate, ferric blue, aluminum powder, copper powder, silver powder, gold powder, barium sulfate, carbon black, and mixtures thereof.

The total amount of inorganic pigments, if present, may vary but is typically about 0.01 to about 20 wt. %, based on the total weigh of the skin tightening composition. The total amount of inorganic pigments may be about 0.01 to about 20 wt. %, about 0.01 to about 18 wt. %, about 0.01 to about 16 wt. %, about 0.01 to about 14 wt. %, about 0.01 to about 12 wt. %, about 0.01 to about 10 wt. %, about 0.01 to about 8 wt. %, about 0.01 to about 6 wt. %, about 0.01 to about 5 wt. %, about 0.01 to about 4 wt. %, about 0.1 to about 10 wt. %, about 0.1 to about 8 wt. %, about 0.1 to about 5 wt. %, or about 0.1 to about 4 wt. %, about 1 to about 20 wt. %, about 1 to about 18 wt. %, about 1 to about 16 wt. %, about 1 to about 14 wt. %, about 1 to about 12 wt. %, about 1 to about 10 wt. %, about 1 to about 8 wt. %, about 2 to about 20 wt. %, about 2 to about 18 wt. %, about 2 to about 16 wt. %, about 2 to about 14 wt. %, about 2 to about 12 wt. %, about 2 to about 10 wt. %, about 2 to about 8 wt. %, about 4 to about 20 wt. %, about 4 to about 18 wt. %, about 4 to about 16 wt. %, about 4 to about 14 wt. %, about 4 to about 12 wt. %, about 4 to about 10 wt. %, about 4 to about 8 wt. %, including ranges and subranges thereof, based on the total weight of the skin tightening composition.

Organic Colorants

The skin tightening compositions may optionally include one or more organic colorants. Non-limiting examples include D & C red no. 19 (CI 45,170), D & C red no. 9 (CI 15,585), D & C red no. 21 (CI 45,380), D & C orange no. 4 (CI 15,510), D & C orange no. 5 (CI 45,370), D & C red no. 27 (CI 45,410), D & C red no. 13 (CI 15,630), D & C red no. 7 (CI 15,850:1), D & C red no. 6 (CI 15,850:2), D & C yellow no. 5 (CI 19,140), D & C red no. 36 (CI 12,085), D & C orange no. 10 (CI 45,425), D & C yellow no. 6 (CI 15,985), D & C red no. 30 (CI 73,360), D & C red no. 3 (CI 45,430), carbon black (CI 77,266), cochineal carmine lake (CI 75,470), natural or synthetic melanin, and aluminium lakes.

The total amount of organic colorants, if present, may vary but is typically about 0.01 to about 20 wt. %, based on the total weigh of the skin tightening composition. The total amount of organic colorants may be about 0.01 to about 20 wt. %, about 0.01 to about 18 wt. %, about 0.01 to about 16 wt. %, about 0.01 to about 14 wt. %, about 0.01 to about 12 wt. %, about 0.01 to about 10 wt. %, about 0.01 to about 8 wt. %, about 0.01 to about 6 wt. %, about 0.01 to about 5 wt. %, about 0.01 to about 4 wt. %, about 0.1 to about 10 wt. %, about 0.1 to about 8 wt. %, about 0.1 to about 5 wt. %, or about 0.1 to about 4 wt. %, about 1 to about 20 wt. %, about 1 to about 18 wt. %, about 1 to about 16 wt. %, about 1 to about 14 wt. %, about 1 to about 12 wt. %, about 1 to about 10 wt. %, about 1 to about 8 wt. %, about 2 to about 20 wt. %, about 2 to about 18 wt. %, about 2 to about 16 wt. %, about 2 to about 14 wt. %, about 2 to about 12 wt. %, about 2 to about 10 wt. %, about 2 to about 8 wt. %, about 4 to about 20 wt. %, about 4 to about 18 wt. %, about 4 to about 16 wt. %, about 4 to about 14 wt. %, about 4 to about 12 wt.

%, about 4 to about 10 wt. %, about 4 to about 8 wt. %, including ranges and subranges thereof, based on the total weight of the skin tightening composition.

Soft Focus Powder

The skin tightening compositions may, optionally, include soft focus powder. Soft focus powders are materials providing a blurring effect, typically due to their light-scattering properties on the skin. Such powders typically have high diffuse reflectance, low specular reflectance, and high diffuse transmittance. Soft focus powders give the skin a smoother appearance, for example, by reducing the difference in luminosity between the valley and the edges of wrinkles and imperfections.

Non-limiting examples of soft focus powders include powders of natural or synthetic origin such as mica, titanated mica, alumina, titanium dioxide, serecite, composite talc/titanium dioxide/alumina/silica powders, polyamide, poly(methyl (meth)acrylate), polyethylene powder, polymethylsilsesquioxane powder, sodium acrylates crosspolymer-2 and a mixture thereof. Additional non-limiting examples include calcium aluminum borosilicate (LUXSIL), PMMA (Microsphere M-100), polyethylene (POLYETHYLENE CI 2080), methyl methacrylate crosspolymer (COVABEADS LH85), nylon-12 (ORGASOL 2002), or ethylene/acrylic acid copolymer (FLOBEADS EA209). In some instances, the skin tightening compositions include at least one soft focus powder selected from the group consisting of silica which may or may not be coated, fumed silica, silica silylate, composite talc/titanium dioxide/alumina/silica powders, polyamide (nylon), poly(methyl (meth)acrylate), polyethylene powder, polymethylsilsesquioxane powder, waxes, such as copernicia cerifera (carnauba) wax, dimethicone/vinyl dimethicone crosspolymer, nylon-12, cellulose, polylactic acid, boron nitride, and a mixture thereof. The copernicia cerifera (carnauba) wax can be provided as a dispersion non water and alcohol. The dimethicone/vinyl dimethicone crosspolymer can be provided as silicone dispersion (INCI: Dimethicone/vinyl dimethicone crosspolymer (and) C12-14 Pareth-12). In some instances, the soft focus powder is (or includes) sodium acrylates crosspolymer-2, which is commercially available as AQUAKEEP 10SH-NFC as sodium acrylates crosspolymer-2 (and) water (and) silica.

The total amount of soft focus powder, if present, can vary but is typically about 0.1 to about 20 wt. %, based on the total weight of the skin tightening composition. In some cases, the total amount of soft focus powder is about 0.1 to about 20 wt. %, about 0.1 to about 18 wt. %, about 0.1 to about 16 wt. %, about 0.1 to about 15 wt. %, about 0.1 to about 14 wt. %, about 0.1 to about 12 wt. %, about 0.1 to about 10 wt. %, about 0.1 to about 5 wt. %, about 1 to about 20 wt. %, about 1 to about 18 wt. %, about 1 to about 16 wt. %, about 1 to about 15 wt. %, about 1 to about 14 wt. %, about 1 to about 12 wt. %, about 1 to about 10 wt. %, or about 1 to about 8 wt. %, about 2 to about 20 wt. %, about 2 to about 18 wt. %, about 2 to about 16 wt. %, about 2 to about 14 wt. %, about 2 to about 12 wt. %, about 2 to about 10 wt. %, about 2 to about 8 wt. %, about 4 to about 20 wt. %, about 4 to about 18 wt. %, about 4 to about 16 wt. %, about 4 to about 14 wt. %, about 4 to about 12 wt. %, about 4 to about 10 wt. %, about 4 to about 8 wt. %, including ranges and subranges thereof, based on the total weight of skin tightening composition.

Methods

The skin tightening compositions are particularly useful for improving the appearance of skin, especially the skin of a human. When the skin tightening compositions are applied to the skin, they provide an immediate improvement to the appearance of the skin that is long lasting. The skin tightening compositions are particularly useful for method of:
  reducing the appearance of fine lines of the skin;
  reducing the appearance of wrinkles of the skin;
  improving the tone of skin and/or improving the evenness of skin tone;
  improving skin softness and/or smoothness;
  reducing the appearance of eye bags;
  reducing the appearance of dark circles around and/or below the eyes;
  reducing the appearance of pores and/or scars; and/or
  increasing the radiance, luminosity, and/or glow of the skin.

Typically, an effective amount of a skin tightening composition is applied to the skin to be treated, for example, the skin of the face and/or neck. In some instances, it may be desirable to apply the skin tightening composition to the skin around (or below) the eyes. The skin tightening compositions can be applied with the hands or may be applies using a brush, sponge, tissue, cotton swab, fabric, or applicator (e.g., pen or other device), etc. The amount needed to achieve the desired effect can be ascertained by the consumer.

Examples of Embodiments

In certain embodiments, skin tightening compositions according to the instant disclosure include:
  about 2 to about 35 wt. %, preferably about 4 to about 35 wt. %, more preferably about 6 to about 25 wt. %, of at least one thickener selected from polyamide-8, styrene ethylene/propylene copolymer, and nylon-611/dimethicone crosspolymer, VP/EICOSENE Copolymer, fumed silica, hydrophobically modified silica, silica silylate, clays or a combination thereof;
  about 1.5 to about 13 wt. %, preferably about 2 to about 11 wt. %, more preferably about 2.5 to about 9 wt. % of at least one filler, such as those chosen from silica sylilate, nylon-12, cellulose, methyl methacrylate crosspolymer, and polymethylsilsesquioxane, and a combination thereof;
  about 5 to about 45 wt. %, preferably about 6 to about 40 wt. %, more preferably about 8 to about 35 wt. %, of at least one hydrophobic film former, such as those chosen from acrylic acid/isobutyl acrylates/isobornyl acrylate copolymer, trimethylsiloxysilicate, acrylates/isobornyl acrylate copolymer, norbornene/tris(trimethylsiloxy)silylnorbornene copolymer, acrylate/polytrimethyl siloxymethacrylate copolymer, $C_{30-45}$ alkyldimethylsilylpolypropylsilsequioxane, trimethylsilsesquioxane, polypropylsilsesquioxane, acrylates/dimethicone copolymer, octylacrylamide/acrylates/butylaminoethyl methacrylate copolymer, VA/butyl maleate/isobornyl acrylate copolymer, acrylates/t-butylacrylamide copolymer, polyvinylpyrrolidone/vinyl acetate copolymer, triacontanyl PVP copolymer, acrylates/dimethylaminoethyl methacrylate copolymer, and a combination thereof; and
  about 20 to about 85 wt. %, preferably about 25 to about 85 wt. %, more preferably about 25 to about 80 wt. %, of at least one volatile hydrocarbon, the volatile hydrocarbon optionally be chosen from isoparaffin, isohexadecane, isododecane, isodecane, undecane, tridecane, dodecane, isohexyl, isodecyl, neopentanoate, or a combination thereof,
  wherein a weight ratio of the at least one hydrophobic film former c) to the at least one thickener a) is 1:2 to 8:1

(hydrophobic film former c): thickener a)), and all weight percentages are based on the total weight of the skin tightening composition.

In additional embodiments, skin tightening compositions according to the instant disclosure include:
- about 2 to about 35 wt. %, preferably about 4 to about 35 wt. %, more preferably about 6 to about 25 wt. %, of at least one thickener selected from polyamide-8, styrene ethylene/propylene copolymer, and nylon-611/dimethicone crosspolymer, VP/EICOSENE Copolymer, fumed silica, hydrophobically modified silica, silica silylate, clays or a combination thereof;
- about 1.5 to about 13 wt. %, preferably about 2 to about 11 wt. %, more preferably about 2.5 to about 9 wt. % of at least one filler, such as those chosen from silica sylilate, nylon-12, cellulose, methyl methacrylate crosspolymer, and polymethylsilsesquioxane, and a combination thereof;
- about 5 to about 45 wt. %, preferably about 6 to about 40 wt. %, more preferably about 8 to about 35 wt. %, of at least one hydrophobic film former, such as those chosen from acrylic acid/isobutyl acrylates/isobornyl acrylate copolymer, trimethylsiloxysilicate, acrylates/isobornyl acrylate copolymer, norbornene/tris(trimethylsiloxy)silylnorbornene copolymer, acrylate/polytrimethyl siloxymethacrylate copolymer, $C_{30-45}$ alkyldimethylsilylpolypropylsilsequioxane, trimethylsilsesquioxane, polypropylsilsesquioxane, acrylates/dimethicone copolymer, octylacrylamide/acrylates/butylaminoethyl methacrylate copolymer, VA/butyl maleate/isobornyl acrylate copolymer, acrylates/t-butylacrylamide copolymer, polyvinylpyrrolidone/vinyl acetate copolymer, triacontanyl PVP copolymer, acrylates/dimethylaminoethyl methacrylate copolymer, and a combination thereof; and
- about 32 to about 85 wt. %, preferably about 35 to about 85 wt. %, more preferably about 35 to about 80 wt. %; of at least one volatile hydrocarbon, wherein the volatile hydrocarbon is optionally chosen from isoparaffin, isohexadecane, isododecane, isodecane, undecane, tridecane, dodecane, isohexyl, isodecyl, neopentanoate, or a combination thereof, wherein the skin tightening composition is anhydrous and a weight ratio of the at least one hydrophobic film former c) to the at least one thickener a) is 1:2 to 8:1 (hydrophobic film former c):thickener a)), and all weight percentages are based on the total weight of the skin tightening composition.

In further embodiments, skin tightening compositions according to the instant disclosure include:
- about 2 to about 35 wt. %, preferably about 4 to about 35 wt. %, more preferably about 6 to about 25 wt. %, of at least one thickener selected from polyamide-8, styrene ethylene/propylene copolymer, and nylon-611/dimethicone crosspolymer, VP/EICOSENE Copolymer, fumed silica, hydrophobically modified silica, silica silylate, clays or a combination thereof;
- about 1.5 to about 13 wt. %, preferably about 2 to about 11 wt. %, more preferably about 2.5 to about 9 wt. % of at least one filler, such as those chosen from silica sylilate, nylon-12, cellulose, methyl methacrylate crosspolymer, and polymethylsilsesquioxane, and a combination thereof;
- about 5 to about 45 wt. %, preferably about 6 to about 40 wt. %, more preferably about 8 to about 35 wt. %, of at least one hydrophobic film former, such as those chosen from acrylic acid/isobutyl acrylates/isobornyl acrylate copolymer, trimethylsiloxysilicate, acrylates/isobornyl acrylate copolymer, norbornene/tris(trimethylsiloxy)silylnorbornene copolymer, acrylate/polytrimethyl siloxymethacrylate copolymer, C30-45 alkyldimethylsilylpolypropylsilsequioxane, trimethylsilsesquioxane, polypropylsilsesquioxane, acrylates/dimethicone copolymer, octylacrylamide/acrylates/butylaminoethyl methacrylate copolymer, VA/butyl maleate/isobornyl acrylate copolymer, acrylates/t-butylacrylamide copolymer, polyvinylpyrrolidone/vinyl acetate copolymer, triacontanyl PVP copolymer, acrylates/dimethylaminoethyl methacrylate copolymer, and a combination thereof;
- about 20 to about 70 wt. %, preferably about 25 to about 70 wt. %, more preferably about 25 to about 60 wt. %, of at least one volatile hydrocarbon, such as those chosen from isoparaffin, isohexadecane, isododecane, isodecane, undecane, tridecane, dodecane, isohexyl, isodecyl, neopentanoate, or a combination thereof;
- about 1 to about 10 wt. %, preferably about 1 to about 8 wt. %, more preferably about 2 to about 6 wt. %, of at least one non-ionic surfactant being optionally chosen from dimethicone (and) peg/ppg-18/18 dimethicone, lauryl peg-9 polydimethylsiloxyethyl dimethicone, cetyl peg/ppg-10/1 dimethicone, peg-30 di polyhydroxystearate, polyglyceryl-4 diisostearate/polyhydroxystearate/sebacate, polyglyceryl-4 isostearate, polyglyceryl-2 dipolyhydroxystearate and a combination thereof;
- about 0.5 to about 10 wt. %, preferably about 1 to about 10 wt. %, more preferably about 1 to about 8 wt. %, of at least one dispersant, such as those chosen from olyoxyethylene glycol ethers or esters (POE/PEG ethers or esters) or polyoxypropylene glycol ethers or esters (PPG ethers or esters), from sugar ethers or esters, from glycerol or polyglycerol ethers or esters and from ethoxylated glyceride esters (POE glyceryl esters), polyhydroxystearic acid, or a combination thereof; and
- about 5 to about 60 wt. %, preferably about 10 to about 60 wt. %, more preferably about 10 to about 50 wt. %, of water, wherein a weight ratio of the at least one hydrophobic film former c) to the at least one thickener a) is 1:2 to 8:1 (hydrophobic film former c):thickener a)), and wherein the skin tightening composition is an emulsion, and all weight percentages are based on the total weight of the skin tightening composition.

EXAMPLES

Implementation of the present disclosure is provided by way of the following examples. The examples serve to illustrate the technology without being limiting in nature.

Example 1

Anhydrous Skin Tightening Compositions

Seven skin tightening compositions (Example Formulas A-G) were prepared in accordance with the formulations shown in Table 1, below.

TABLE 1

| | | INCI | A (wt. %) | B (wt. %) | C (wt. %) | D (wt. %) | E (wt. %) | F (wt. %) | G (wt. %) |
|---|---|---|---|---|---|---|---|---|---|
| a) | Thickener | POLYAMIDE-8 | 12.5 | 16.67 | | | | | |
| | | STYRENE-ETHYLENE/PROPYLENE COPOLYMER | | | 3.12 | 6.25 | 8.33 | 12.5 | 8.33 |
| b) | Filler | SILICA SILYLATE (AIRLICA KTL-10) | 3.13 | 3.13 | 3.13 | 3.13 | 3.13 | 3.13 | |
| | | SILICA SILYLATE (DOW CORNING VM-2270 AEROGEL) | | | | | | | |
| | | POLYMETHYLSILSESQUIOXANE | | | | | | | 6.25 |
| c) | Film former | NORBORNENE/TRIS(TRIMETHYLSILOXY)SILYLNORBORNENE COPOLYMER | | | | | | | 12.5 |
| | | ACRYLATES/ISOBORNYL ACRYLATE COPOLYMER | 12.5 | 12.5 | 12.5 | 12.5 | 12.5 | 12.5 | |
| d) | Volatile hydrocarbon | C8-9 ISOPARAFFIN | 33.58 | 31.21 | 38.75 | 37.13 | 35.84 | 33.58 | 41.12 |
| | | ISODODECANE | 38.3 | 36.5 | 42.5 | 41 | 40.2 | 38.3 | 31.8 |

Example 2

Evaluation of Anhydrous Skin Tightening Compositions

Films were formed from the skin tightening compositions of Example Formulas A-G and evaluated to the level of gloss, transparence, and haze for each film. Specifically, films for Example Formulas A-G were made using a draw down bar at 8" to cast a sample of Example Formulas A-G on a transparent plastic substrate. The sample was allowed to dry on the substrate for 3 hours. Each of the samples of Example Formulas A-G produced a film on the substrates. A BYK Glossmeter was used to measure the gloss and mattness of each film formed from Example Formulas A-E at an angle of 60°.

A BYK Haze-Guard instrument was used to measure the transparency and the haze of each of the films of Example Formulas A-G. The results of the evaluation of the gloss, transparence, and haze are provided in Table 2.

TABLE 2

| | A | B | D | E | F | G |
|---|---|---|---|---|---|---|
| Transparency (%) | 96.9 | 96.6 | 93.3 | 92.4 | 91.8 | 93.5 |
| Haze (%) | 94.6 | 94.6 | 90.4 | 89.7 | 88.4 | 94.9 |
| Gloss at 60° | 13.1 | 13.1 | 6 | 6.2 | 6.6 | 9 |

The transparency, haze, and gloss was not determined for Example Formula C. Each of the films formed from Example Formulas A, B, and D-G exhibited excellent transparence for non-pigmented skin-tightening compositions. As discussed herein, Example Formulas A, B, D, and G exhibited excellent haze characteristics as the level of haze is preferably at least 90% and up to 97% for non-pigmented skin-tightening compositions. Example Formulas D-G exhibited excellent gloss properties, with gloss measurements at an angle of 60° being less than 10.

Example 3

Anhydrous Skin Tightening Compositions with Pigments

Four skin tightening compositions (Example Formulas H-K) were prepared in accordance with the formulations shown in Table 3.

TABLE 3

| | | INCI | H (wt. %) | I (wt. %) | J (wt. %) | K (wt. %) |
|---|---|---|---|---|---|---|
| a) | Thickener | STYRENE-ETHYLENE/PROPYLENE COPOLYMER | 8.33 | 8.33 | 8.33 | 8.33 |
| b) | Filler | SILICA SILYLATE (AIRLICA KTL-10) | 3.13 | 3.13 | 3.13 | 3.13 |
| c) | Film former | ACRYLATES/ISOBORNYL ACRYLATE COPOLYMER | 12.50 | 12.50 | 12.50 | 12.50 |
| d) | Volatile hydrocarbon | C8-9 ISOPARAFFIN | 30.84 | 37.99 | 25.84 | 32.99 |
| | | ISODODECANE | 40.20 | 33.05 | 40.20 | 33.05 |
| h) | Pigment | ALUMINA (and) TITANIUM DIOXIDE (and) TRIETHOXYCAPRYLYLSILANE | 4.22 | 4.22 | 8.43 | 8.43 |
| | | ALUMINA (and) IRON OXIDES | 0.78 | 0.78 | 1.57 | 1.57 |

TABLE 3-continued

| INCI | H (wt. %) | I (wt. %) | J (wt. %) | K (wt. %) |
|---|---|---|---|---|
| (and) TRIETHOXYCAPRYLYLSILANE (and) SILICA DIMETHYL SILYLATE | | | | |

Example 4

Evaluation of Anhydrous Skin Tightening Compositions with Pigments

Films were formed from the skin tightening compositions of Example Formulas H-K and evaluated to the level of gloss, transparence, and haze for each film. The films for Example Formulas H-K were prepared and evaluated according to the procedures discussed in Example 2. The results of the evaluation are provided in Table 4.

TABLE 4

| | H | I | J | K |
|---|---|---|---|---|
| Transparency (%) | 28.8 | 30.2 | 11.9 | 13.5 |
| Haze (%) | 99.8 | 99.7 | 99.6 | 99.6 |
| Gloss at 60° | 2.6 | 1.4 | 2.5 | 1.3 |

Example Formulas H-K exhibited excellent gloss properties, with gloss measurements at an angle of 60° being less than 10.

Example 5

Skin Tightening Emulsions

Three skin tightening compositions (Example Formulas L-N) were prepared in accordance with the formulations shown in Table 5, below. The skin tightening compositions of Example Formulas L-N were in the form of an emulsion.

TABLE 5

| | | INCI | L (wt. %) | M (wt. %) | N (wt. %) |
|---|---|---|---|---|---|
| a) | Thickener | POLYAMIDE-8 | | 12.50 | |
| | | STYRENE-ETHYLENE/PROPYLENE COPOLYMER | 8.33 | | 8.33 |
| b) | Filler | SILICA SILYLATE (AIRLICA KTL-10) | 3.13 | 3.13 | 3.13 |
| c) | Film former | ACRYLATES/POLYMETHYLSILOXYMETHACRYLATE COPOLYMER | | | 12.50 |
| | | ACRYLATES/ISOBORNYL ACRYLATE COPOLYMER | 12.50 | 12.50 | |
| d) | Volatile hydrocarbon | C8-9 ISOPARAFFIN | 6.89 | 4.62 | 14.04 |
| | | ISODODECANE | 40.20 | 38.30 | 33.05 |
| e) | Surfactant | LAURYL PEG-9 POLYDIMETHYLSILOXYETHYL DIMETHICONE | 1.50 | 1.50 | 1.50 |
| | | DIMETHICONE (and) PEG/PPG-18/18 DIMETHICONE | 2.00 | 2.00 | 2.00 |
| f) | Dispersant | POLYHYDROXYSTEARIC ACID | 2.00 | 2.00 | 2.00 |
| g) | Water | WATER | 20.00 | 20.00 | 20.00 |
| | Misc. | MAGNESIUN SULFATE; PHENOXYETHANOL; CARYLYL GLYCOL; and DENATURED ALCOHOL | 3.45 | 3.45 | 3.45 |

Example 6

Evaluation of Skin Tightening Emulsions

Films were formed from the skin tightening compositions of Example Formulas L-N and evaluated to the level of gloss, transparence, and haze for each film. The films for Example Formulas L-N were prepared and evaluated according to the procedures discussed in Example 2. The results of the evaluation are provided in Table 6, below.

TABLE 6

| | L | M | N |
|---|---|---|---|
| Transparency (%) | 92.2 | 94.2 | 94.2 |
| Haze (%) | 90 | 92.5 | 93.9 |
| Gloss at 60° | 10.6 | 14.8 | 9.1 |

Each of the films formed from Example Formulas L-N exhibited excellent transparence for non-pigmented skin-tightening compositions. Example Formulas M and N exhibited excellent haze characteristics as the level of haze is preferably at least 90% and up to 97% for non-pigmented skin-tightening compositions. Example L exhibited good haze characteristics. Example Formula N exhibited excellent gloss properties, with gloss measurements at an angle of 60° being less than 10. Example Formula L exhibited only suitable gloss properties at an angle of 60°.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" are used in their open, non-limiting sense.

The terms "a," "an," and "the" are understood to encompass the plural as well as the singular. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The expression "one or more" means "at least one" and thus includes individual components as well as mixtures/combinations.

Other than in the operating examples, or where otherwise indicated, all numbers expressing quantities of ingredients and/or reaction conditions may be modified in all instances by the term "about," meaning within +/−5% of the indicated number.

Some of the various categories of components identified may overlap. In such cases where overlap may exist and the composition includes both components (or the composition includes more than two components that overlap), an overlapping compound does not represent more than one component. For example, a particular component may be considered both a thickener and a filler. If a particular composition includes both a thickener and a filler, a single ingredient will serve as only the thickener or only the filler (a single ingredients cannot serve as both the thickener and the filler).

The salts referred to throughout the disclosure may include salts having a counter-ion such as an alkali metal, alkaline earth metal, or ammonium counter-ion. This list of counter-ions, however, is non-limiting.

The term "treat" (and its grammatical variations) as used herein refers to the application of the compositions of the present disclosure onto the surface of keratinous substrates such as skin, in particular, the skin of the head, face, and neck.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc. All ranges and values disclosed herein are inclusive and combinable. For examples, any value or point described herein that falls within a range described herein can serve as a minimum or maximum value to derive a sub-range, etc.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material. All of the components set forth herein may be optionally included or excluded from the compositions/method/kits. When excluded, the compositions/methods/kits may be free or essentially free of the component. For example, a particular composition may be free or essentially free of alkoxylated compounds, for example, ethoxylated thickeners and/or ethoxylated surfactants. Likewise, a particular composition may be free or essentially free of sulfates, such as sulfate surfactants.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:

1. A skin tightening composition comprising:
   (a) about 3 to about 20 wt. % of at least one thickener chosen from polyamide-8, styrene ethylene/propylene copolymer, VP/eicosene copolymer, and a combination thereof;
   (b) about 1.5% to about 13 wt. % of at least one filler is chosen from silica silylate, polymethylsilsesquioxane, and a combination thereof;
   (c) about 5 to about 45 wt. % of acrylates/isobornyl acrylate copolymer;
   (d) about 32 to about 85 wt. % of at least one volatile hydrocarbon,
   wherein the skin tightening composition comprises less than 1 wt. % of water,
   the skin tightening composition has a weight ratio of the acrylates/isobornyl acrylate copolymer (c) to the at least one thickener (a) is 1:1.5 to 8:1 ((c):(a)), and
   wherein, all weight percentages are based on the total weight of the skin tightening composition.

2. The skin tightening composition of claim 1 free of dimethicone crosspolymer.

3. A skin tightening composition comprising:
   (a) about 3 to about 20 wt. % of at least one thickener chosen from polyamide-8, styrene ethylene/propylene copolymer, VP/eicosene copolymer, and a combination thereof;
   (b) about 1.5 to about 13 wt. % of at least one filler chosen from silica sylilate, polymethylsilsesquioxane, and a combination thereof;
   (c) about 5 to about 45 wt. % of acrylates/isobornyl acrylate copolymer;

(d) about 20 to about 70 wt. % of at least one volatile hydrocarbon;
(e) about 1 to about 10 wt. % of at least one non-ionic surfactant;
(f) about 0.5 to about 10 wt. % of at least one dispersant; and
(g) about 15 to about 60 wt. % of water;
   wherein a weight ratio of the acrylates/isobornyl acrylate copolymer (c) to the at least one thickener (a) is 1:1.5 to 8:1 ((c):(a)), and
   wherein the skin tightening composition is a water in oil emulsion, and all weight percentages are based on the total weight of the skin tightening composition.

4. The skin tightening composition of claim 3 free of dimethicone crosspolymer.

5. The skin tightening composition of claim 3, comprising from about 20 to about 60 wt. % water.

* * * * *